(12) United States Patent
Schaefer et al.

(10) Patent No.: US 12,296,083 B2
(45) Date of Patent: May 13, 2025

(54) SYSTEM AND METHOD FOR DETECTING VENOUS NEEDLE DISLODGEMENT

(71) Applicants: AWE Technologies LLC, Bay Shore, NY (US); Fresenius Medical Care Holdings, Inc., Waltham, MA (US)

(72) Inventors: Robert Schaefer, Bay Shore, NY (US); Gareth T. Schaefer, Bay Shore, NY (US); Scott Macintosh, Bay Shore, NY (US); Dipen N. Sinha, Bay Shore, NY (US); Peter G. Espina, Bay Shore, NY (US); Martin J. Crnkovich, Waltham, MA (US)

(73) Assignees: AWE Technologies LLC, Bay Shore, NY (US); Fresenius Medical Care Holdings, Inc., Waltham, MA (US)

( * ) Notice: Subject to any disclaimer, the term of this patent is extended or adjusted under 35 U.S.C. 154(b) by 900 days.

(21) Appl. No.: 17/364,156

(22) Filed: Jun. 30, 2021

(65) Prior Publication Data

US 2022/0001090 A1    Jan. 6, 2022

Related U.S. Application Data

(60) Provisional application No. 63/047,727, filed on Jul. 2, 2020.

(51) Int. Cl.
*A61M 1/36* (2006.01)
*A61M 1/16* (2006.01)

(52) U.S. Cl.
CPC ........ *A61M 1/3656* (2014.02); *A61M 1/1605* (2014.02); *A61M 1/3626* (2013.01);
(Continued)

(58) Field of Classification Search
CPC ........ A61M 2205/3375; A61M 1/1605; A61M 1/3626; A61M 2205/13; A61M 1/3656;
(Continued)

(56) References Cited

U.S. PATENT DOCUMENTS 4,607,520 A * 8/1986 Dam ............... G01N 29/449
73/61.79
4,923,598 A * 5/1990 Schal ............... B01D 61/22
210/90

(Continued)

FOREIGN PATENT DOCUMENTS

WO    2021053201 A1    3/2021

OTHER PUBLICATIONS

International Search Report and Written Opinion, PCT/US2021/039744, dated Oct. 13, 2021, 12 pages.
(Continued)

*Primary Examiner* — Phillip A Gray
*Assistant Examiner* — Forrest Blake Dipert
(74) *Attorney, Agent, or Firm* — Potomac Law Group, PLLC

(57) ABSTRACT

In one aspect, a method and system for detecting a change in fluid dynamics of a fluid flowing through an extra-corporeal circuit is disclosed, which includes establishing an acoustic wave resonance across a transverse dimension of at least a portion of a line associated with the extra-corporeal circuit through which the fluid flows, monitoring a phase signal of the resonant acoustic wave, and identifying occurrence of a change in fluid dynamics of the flowing fluid when the observed phase signal of the resonant acoustic wave indicates a deviation from the expected fluid flow signature. The change in fluid dynamics can be used to indicate a venous needle dislodgement event.

15 Claims, 35 Drawing Sheets

(52) U.S. Cl.
    CPC ............... *A61M 2205/13* (2013.01); *A61M 2205/3334* (2013.01); *A61M 2205/3344* (2013.01); *A61M 2205/3375* (2013.01)

(58) Field of Classification Search
    CPC ...... A61M 2005/1588; A61M 2205/14; A61M 2205/15; A61M 2039/1005; A61M 2205/3334; A61M 1/1609
    See application file for complete search history.

(56) References Cited

U.S. PATENT DOCUMENTS

| | | | |
|---|---|---|---|
| 8,535,522 B2 | 9/2013 | Fulkerson et al. | |
| 10,940,252 B2 | 3/2021 | Toyoda et al. | |
| 2002/0091350 A1* | 7/2002 | Belson | B01D 63/16 210/646 |
| 2007/0219597 A1* | 9/2007 | Kamen | A61B 5/150358 604/404 |
| 2009/0082676 A1 | 3/2009 | Bennison | |
| 2012/0150091 A1* | 6/2012 | Roger | A61M 1/3607 604/6.16 |
| 2012/0271160 A1* | 10/2012 | Buckberry | A61M 5/16836 600/424 |
| 2012/0271161 A1* | 10/2012 | Buckberry | A61M 5/16836 604/111 |
| 2012/0289928 A1* | 11/2012 | Wright | A61M 1/3626 604/67 |
| 2013/0204174 A1 | 8/2013 | Olde et al. | |
| 2014/0262252 A1* | 9/2014 | Slepicka | E21B 47/095 166/255.2 |
| 2017/0108471 A1* | 4/2017 | Sturtevant | G01N 29/227 |
| 2017/0173253 A1* | 6/2017 | Funkhouser | A61M 1/3656 |
| 2019/0217030 A1* | 7/2019 | Burgess | A61M 16/109 |

OTHER PUBLICATIONS

International Preliminary Report on Patentability, PCT/US2021/039744, dated Dec. 13, 2022, 7 Pages.

International Search Report and Written Opinion mailed Feb. 3, 2025 for International Patent Application No. PCT/US2024/052736.

\* cited by examiner

SECTION C-C
SCALE 1 : 1

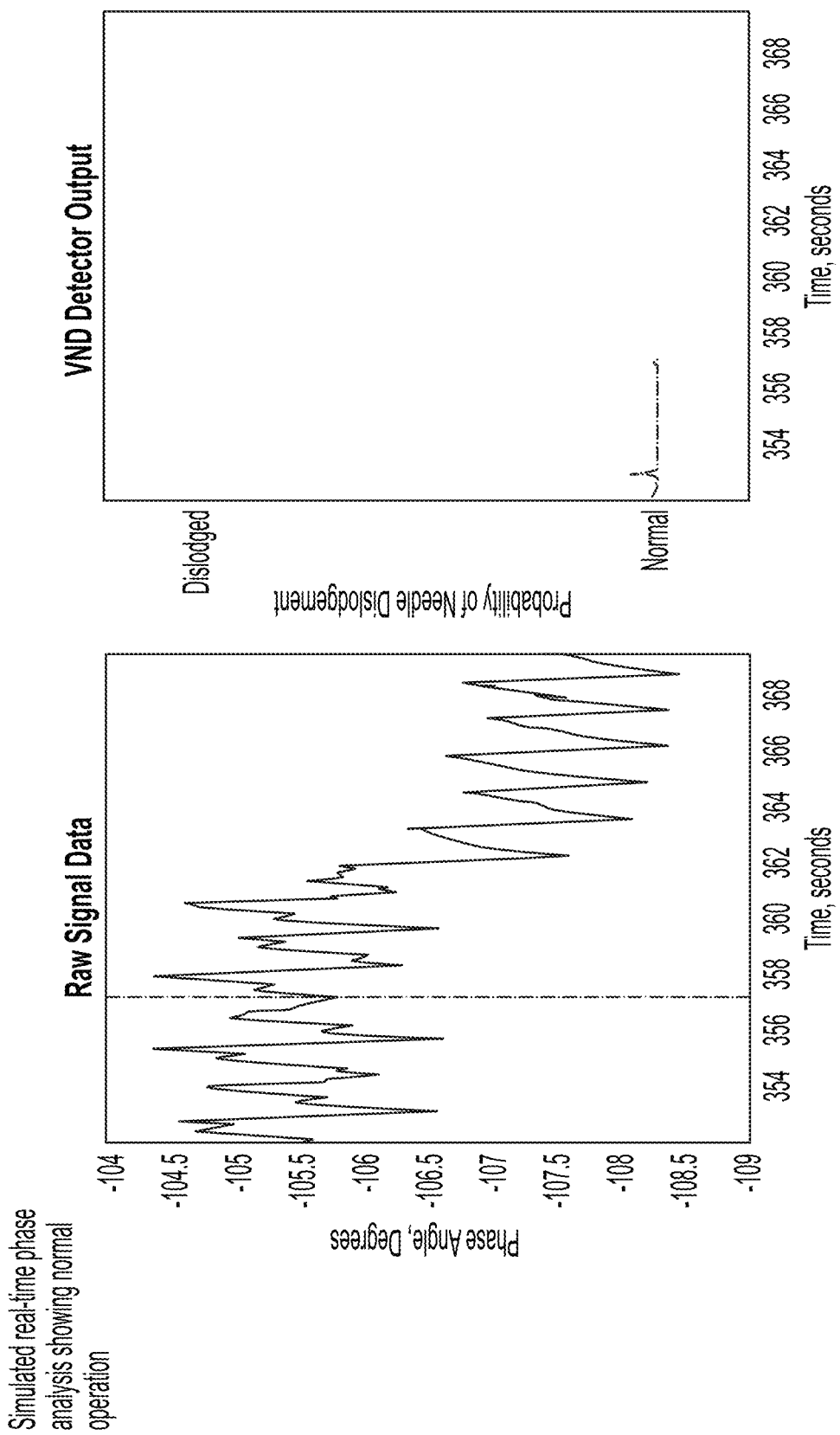

| VND-04 Study Visit 2: 02/24/2021 | | | |
|---|---|---|---|
| 10:32 | Sensor attached | | |
| 10:33 | Treatment started | | Pump rate: 350 |
| 10:37 | Heparin administered | | |
| 10:45 | Hectorol administered | | |
| 10:46 | Arterial pressure alarm | | |
| 12:28 | Arterial Pressure Alarm | | |
| 1:14 | UF stopped | | |
| 2:34 | Treatment finished | | |

FIG. 18A

| VND-04 Study Visit 2: 02/24/2021 | | | |
|---|---|---|---|
| 10:32 | Sensor attached | | |
| 10:33 | Treatment started | | Pump rate: 350 |
| 10:37 | Heparin administered | | |
| 10:45 | Hectorol administered | | |
| 10:46 | Arterial pressure alarm | | |
| 12:28 | Arterial Pressure Alarm | | |
| 1:14 | UF stopped | | |
| 2:34 | Treatment finished | | |

FIG. 21A

| VND-04 Study Visit 2: 02/24/2021 | | | |
|---|---|---|---|
| 10:32 | Sensor attached | | |
| 10:33 | Treatment started | | Pump rate: 350 |
| 10:37 | Heparin administered | | |
| 10:45 | Hectorol administered | | |
| 10:46 | Arterial pressure alarm | | |
| 12:28 | Arterial Pressure Alarm | | |
| 1:14 | UF stopped | | |
| 2:34 | Treatment finished | | |

FIG. 22A

SYSTEM AND METHOD FOR DETECTING VENOUS NEEDLE DISLODGEMENT

CROSS-REFERENCE TO RELATED APPLICATION

The present application claims priority to U.S. Provisional Application No. 63/047,727 filed on Jul. 2, 2020, which application is incorporated herein by reference in its entirety.

BACKGROUND

The present disclosure is generally directed to systems and methods for detecting a change in fluid dynamics of a fluid flowing in an extra-corporeal circuit, and more particularly to such systems and methods that can be employed to detect venous needle dislodgement (VND) in a dialysis system.

Venous needle dislodgement (VND) during dialysis is a rare event. However, if VND is not detected quickly, it can lead to fatal blood loss in only a few minutes. For example, patients with a normal blood volume of 3-5 L subjected to the normal extracorporeal blood flow rate of 200-500 ml/min during dialysis, will likely suffer from fatal blood loss within 2-5 minutes after a VND. The reported number of VNDs per treatment falls within a wide range, from 0.0008% to 0.1% with an estimate that 10-33% of the VNDs lead to death.

A number of different approaches for detecting VNDs have been implemented. But these conventional approaches suffer from a number of shortcomings. In some such conventional approaches, the venous line pressure is measured in various ways to try to detect a VND based on an abrupt decrease in the venous line pressure. However, such pressure-monitoring approaches are not robust because a VND leads to only a small pressure change in the venous return line. Conventional pressure monitoring systems with sufficient sensitivity to detect such small pressure changes have been utilized, but such systems require sufficient damping or averaging to reduce noise in the measurement, which would otherwise adversely affect the systems' response time. In addition, such systems require sensor contact with the blood. Moreover, these systems typically suffer from many false positives, thus increasing the burden of monitoring and addressing false alarms.

Another approach is to place wetness detectors at or near a patient's access point, which would send an alert after blood has leaked and collected at the detector. Wetness detectors are also less than optimal because a misplaced detector can defeat such a system and the path of a leak cannot always be reliability predicted. Mechanical tube constriction devices are also less than optimal because of the potential for improper implementation.

Thus, there is a need for a reliable, robust, and cost-effective solution for detecting VNDs.

SUMMARY

In one aspect, a method of detecting a change in the fluid dynamics of a fluid flowing through an extra-corporeal circuit is disclosed, which includes establishing an acoustic wave resonance across at least a portion of a line associated with the extra-corporeal circuit through which the fluid flows, monitoring a phase signal of the resonant acoustic wave, and identifying occurrence of a change in the fluid dynamics of the flowing fluid when the observed phase signal of the resonant acoustic wave indicates a deviation from an expected phase signature associated with the fluid flow.

The term "phase signature," as used herein, refers to a temporal variation of the phase signal that is indicative of a normal (desired) fluid dynamics associated with the fluid flow. For example, such a "phase signature" can refer to a periodic variation of the phase signal (e.g., a periodic variation of the phase signal due to a patient's heartbeats) and/or an average phase signal value.

In embodiments discussed below, the acoustic standing wave is established across a transverse (e.g., across the diameter) of the line. More generally, the acoustic wave can be established along a dimension of the line that forms a non-zero angle relative to an axial dimension of the line, where the axial dimension is substantially parallel to the direction of fluid flow.

The step of establishing the resonant acoustic wave can include transmitting an acoustic wave into a portion of the line, e.g., along a transverse dimension thereof (e.g., along the diameter of the line), and detecting at least a portion of the acoustic wave after its passage through the flowing fluid. The phase signal can correspond to a difference between a phase of the transmitted acoustic wave and a phase of the detected acoustic wave.

In some embodiments, the extra-corporeal circuit includes an extra-corporeal dialysis circuit (such as a hemodialysis circuit) and the line is a venous return line of the extra-corporeal dialysis circuit.

In some embodiments, the expected phase signature includes a phase signature associated with heartbeats of a patient coupled to the extra-corporeal circuit, e.g., a venous return line of a hemodialysis circuit.

In some embodiments, the change in the fluid dynamics is caused by at least partial dislodgement of a venous return line. For example, the deviation of the monitored phase relative to the expected phase signature can include a substantial change (e.g., disappearance) of the phase signature, indicating a substantially complete dislodgement of the venous return line.

In some embodiments, the acoustic wave is monochromatic. By way of example, in such embodiments, the acoustic wave can have a frequency in a range of about 1 to about 20 MHz, e.g., in a range of about 1 MHz to about 5 MHz. The acoustic wave can be excited by any periodic waveform (e.g., sine-wave, square wave, etc.,) with a chosen frequency in the frequency range.

In some embodiments, the deviation of the monitored phase signal relative to the expected phase signature can be caused by passage of one or more air bubbles through the portion of the lines across which the acoustic wave resonance is established. In some cases, the passage of one or more air bubbles through the line can be detected via the detection of a significant drop in amplitude and/or a large phase shift of the acoustic signal. In some embodiments, a change of the phase signal occurring over a time period less than about 0.1 second can be indicative of the passage of one or more air bubbles through the sensing portion of the device.

In some embodiments, the flow rate of the fluid passing through the extra-corporeal line can be adjusted in response to the detection of the air bubbles within the fluid flow. Typically, the flow rate of the blood pump needs to be slowed down or stopped altogether depending on the amount of bubbles detected. For example, in some such embodiments, the fluid can be blood, such as blood flowing in the extra-corporeal line of a dialysis system. In such an embodiment, in response to the detection of air bubbles, the flow rate of the blood can be reduced while the phase signal is monitored until no bubbles are detected. In some embodiments, a feedback control signal based on the phase output signal can be generated and applied to the blood pump to adjust the operation of the blood pump in response to the detection of one or more air bubbles flowing through the sensing portion of the device.

In some embodiments, the deviation of the monitored phase signal relative to the expected phase signature can be caused by a change in hydrodynamic pressure of the fluid flowing through the extra-corporeal circuit. In some such embodiments, a change in the hydrodynamic pressure of the fluid can cause a change in the transverse dimension of at least a portion of the line, thus contributing to the shift of the monitored phase relative to the expected phase signature.

In some embodiments, the deviation of the monitored phase from the expected phase signature can indicate an inconsistent flow rate of the fluid through the extra-corporeal circuit.

In some embodiments in which the fluid is blood, the deviation in the monitored phase relative to the expected phase signature can be caused by at least one blood clot.

In some embodiments, the line of the extra-corporeal circuit can be in the form of a tubing. By way of example, such a tubing can provide a venous return line of the extra-corporeal circuit of a hemodialysis system and the change in the deviation in the monitored phase relative to the expected phase signature can be at least partially caused by periodic expansion and contraction of the tubing as the fluid passes through the tubing.

The deviation of the measured phase from an expected phase signature can be observed, e.g., by comparing the measured phase with a previously-obtained phase signature corresponding to an expected fluid dynamics of a normal fluid flow. In some embodiments, an event, e.g., a venous needle dislodgement (VND), can result in a substantial disappearance of the phase signal signature, thereby indicating the occurrence of the event.

In a related aspect, a method of detecting a change in fluid dynamics of a fluid (e.g., blood) flowing in a line that is in fluid communication with a blood vessel of a patient is disclosed, which includes establishing a resonant standing acoustic wave in a portion of the line, monitoring a phase signal of the resonant standing acoustic wave, and identifying occurrence of a change in the fluid dynamics of the flowing fluid when the observed phase of the resonant acoustic wave (i.e., a difference between the phase of the transmit and receive acoustic signals) indicates a deviation from an expected phase signature associated with normal fluid dynamics of the flowing fluid. In some embodiments, such a deviation can correspond to a substantial (or complete) disappearance of the phase signal.

In some embodiments, the phase deviation can be caused by passage of one or more air bubbles through the line.

In some embodiments, the line is a venous return line of a dialysis system and the deviation of the phase signal with respect to an expected phase signature associated with the blood flow through the line can be caused by at least partial dislodgement of the venous return line. For example, a substantial disappearance of the phase signal unique characteristics (phase signal signature) can indicate a substantially complete dislodgement of the venous return line.

In some embodiments, a tubing having a lumen through which blood can flow forms the venous return line. In some cases, such a tubing can have an inner diameter (ID) in a range of about 3 mm to about 5 mm (e.g., 3.5 mm (pediatric) or 4.3 mm (standard) and an outer diameter (OD) in a range of about 5 mm to about 7 mm (e.g., 5.5 mm (pediatric) or 6.8 mm (standard)) Further, in some cases, the tubing can undergo periodic expansion and contraction, e.g., due to the pulsation of blood circulating through the line, and such periodic expansion and contraction can lead to the generation of a phase signature. As noted above and discussed in more detail below, a change in the phase signature can indicate the occurrence of an event, e.g., a partial or complete dislodgement of a venous return line of a dialysis system.

The tubing can be formed of a variety of different materials, such as polyurethane, glass, polyvinyl chloride, silicone, and the like.

The establishment of an acoustic standing wave across the line (e.g., across the diameter of a tubing) can be achieved by coupling two acoustic transducers on opposed sides of the line, where one acoustic transducer (e.g., a piezoelectric device) can generate an acoustic wave and transmit the wave into the line along a transverse dimension thereof and the other acoustic transducer can detect at least a portion of the acoustic wave transmitted through the tubing wall and the flowing fluid (e.g., the flowing blood). In some embodiments, the acoustic transmitter and/or detector can be releasably coupled to the line.

In a related aspect, a system for detecting a change in fluid dynamics of a fluid circulating in a line associated with an extra-corporeal circuit is disclosed, which includes an acoustic wave transmitter for transmitting an acoustic wave into a lumen of the line, e.g., across a transverse dimension thereof, such that the acoustic wave travels through a portion of the fluid traversing through the lumen. The system can further include a detector for detecting at least a portion of the acoustic wave after its passage through the fluid, and a phase detector for measuring a phase signal indicative of a phase difference between the transmitted acoustic wave and the detected acoustic wave. A comparator circuit can be employed to compare the measured phase signal with an expected phase signature associated with the fluid flow, where a deviation identified by the comparator between the measured phase signal and the expected phase signature can indicate the occurrence of a change in the fluid dynamics of the flowing fluid. In some embodiments, the system can include an analyzer for correlating the observed phase deviation to an event associated with the fluid dynamics causing the phase shift.

By way of example, the analyzer can be configured to analyze the phase deviation so as to identify the event associated with the phase deviation as any of (1) passage of one or more air bubbles, (2) passage of one or more blood clots, and (3) at least partial dislodgement of at least a portion of the line from an expected position.

In some embodiments, the acoustic transmitter can generate acoustic waves with a frequency in a range of about 1 to about 20 MHz, e.g., in a range of about 5 MHz to about 10 MHz. In some such embodiments, the acoustic wave is monochromatic.

In some embodiments, the extra-corporeal circuit can be an extra-corporeal circuit of a dialysis system (e.g., a hemodialysis system) and the analyzer can be configured to identify a deviation of the phase signal relative to an expected phase signature, which is indicative of at least partial dislodgement of the venous return line. For example, the analyzer can be configured to correlate a substantial change of the phase signal (e.g., a substantial disappearance of the unique characteristics of the phase signal associated with normal fluid dynamics) with a substantially complete dislodgement of the venous return line.

In some embodiments, the acoustic wave transducers can be proximate to and/or releasably coupled to the line, e.g., a venous return line of a dialysis system. By way of example, a coupling element (e.g., a clamp) can be employed for releasable coupling of the acoustic transducers to the line.

In some embodiments, such a clamp can include two arms that are spring-biased relative to one another to allow releasable holding of a portion of the extra-corporeal line between their tips. In some embodiments, the tips of the clamp arms can include recesses, each of which can receive an element (e.g., a plastic element), which can be configured to receive one of the acoustic transducers, as discussed in more detail below.

For example, each plastic element can include a recess into which a housing containing one of the acoustic transducers can be positioned. Further, each plastic element can include a pair of projections that can come into contact with the respective pair of projections on the other plastic element when a portion of the venous return line is held between the clamp arms. This can facilitate holding the line between the arms of the clamp.

In some embodiments, the housing for each acoustic transducer can include a body having a lumen that extends from a proximal end of the body to its distal end. In some embodiments, the distal end of the housing can exhibit a widening taper that terminates at the distal surface of the body. Each housing can accommodate a piezoelectric transducer for transmitting or receiving an acoustic signal. A plurality of conductive elements extend through the lumens of the housings and are electrically coupled to the transducers to supply electrical power to the transmit transducer and to transmit one or more detection signals generated by the receive transducer to a signal processing/analysis module, as discussed in more detail below. In some embodiments, the lumens of the two transducer housings can be at least partially filled with an epoxy, e.g., a tungsten epoxy.

In some embodiments, a dialysis system is disclosed, which includes a dialyzer, an arterial line for providing a path for blood flow from a patient's circulatory system to an inlet port of the dialyzer, a venous blood line for providing a path for flow of blood exiting the dialyzer to the patient's circulatory system, and an acoustic sensor removably coupled to the venous blood line. The acoustic sensor can be configured to establish an acoustic standing wave along a transverse dimension of a portion of the venous blood line and to monitor a phase signal associated with the acoustic standing wave. A deviation in the monitored phase signal relative to an expected phase signature can be employed to identify at least a partial dislodgement of the venous return line. In some such embodiments, a dislodgement of the venous return line can result in a substantial disappearance of unique signature of the phase signal (e.g., a signature corresponding to a patient's heartbeats).

In some embodiments, the acoustic sensor can include a transmitter for generating an acoustic wave and a detector for detecting at least a portion of the acoustic wave after its passage through a portion of the venous line. The transmitter and the detector can be positioned on opposite sides of the venous return line. The system can further include a phase comparator for determining a phase shift between the transmitted and detected acoustic waves, thereby generating a phase signal (herein also referred to as a phase difference signal) that can be employed, in a manner disclosed herein, for detecting venous line dislodgement.

In some embodiments, an acoustic sensor as described herein may be configured to be positioned at the arterial or venous drip chambers which are found on available hemodialysis (HD) machines. The diameter of these chambers may range, for example, from about 18 mm to about 30 mm.

Further understanding of various aspects of the present teachings can be obtained by reference to the following detailed description in conjunction with the associated drawings, which are described briefly below.

BRIEF DESCRIPTION OF THE DRAWINGS

FIG. 10A shows a simulated phase signal corresponding to normal operation of an extra-corporeal dialysis system;

FIG. 10B shows a probability for a VND event derived based on the phase signal depicted in FIG. 10A;

FIG. 18A shows a portion of a daily log of the dialysis treatment with ultra filtration (UF) pump turned on and off;

FIG. 21A shows a portion of a daily log of the dialysis treatment with an injection of heparin introduced;

FIG. 22A shows a portion of a daily log of the dialysis treatment with an injection of medication (e.g., Hectorol) introduced follow by a pump shut down;

DETAILED DESCRIPTION

In one aspect, the present disclosure is directed to a VND detection system and method that can continually sense the venous pulse by employing a highly sensitive phase detector circuit. In some embodiments, an absence (or a substantial absence) of a phase signature may be used to detect a VND event. By way of example, the sensor can be incorporated as part of a dialysis system and can be configured for coupling (e.g., releasably) to the disposable venous blood line. The sensor can include a transmitter configured to create an ultrasonic standing wave that travels across the venous blood line to the receiver element on the opposite side of the venous blood line and reflects back from the tube boundary. A receiver transducer is used to detect the standing wave established within the diameter of the fluid-filled tube, thus allowing the monitoring of the phase shift between the transmitted signal and the received signal.

A change in the fluid dynamics of the blood flow can be monitored by measuring this phase shift between the transmitted and received signal of the standing wave (a resonance condition) caused by the venous blood flow relative to an expected phase signature, e.g., one generated due to the patient's heartbeats. The measured phase shift varies with the blood flow and is sensitive enough to detect minute variations in flow conditions originating from heartbeat or operating pumps. Although in the following discussion various features of the present teachings are described in connection with the detection of VND, it should be understood that the present teachings are generally applicable for detecting changes in the sound speed or fluid dynamics of a fluid (e.g., a liquid) flowing through other extra-corporeal circuits, such as a lung-heart machine.

Figure 1:
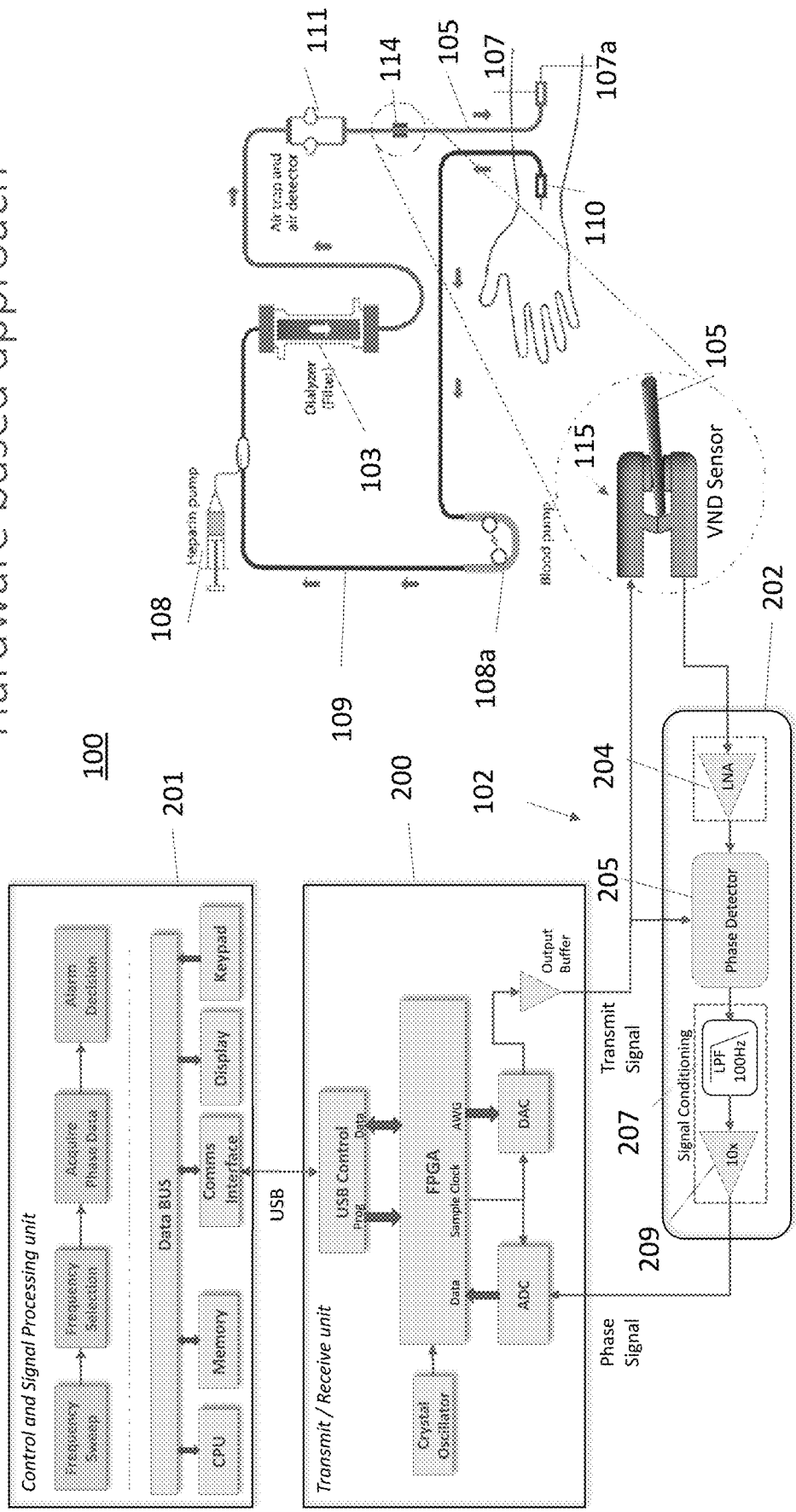
FIG. 1 is a schematic representation of a dialysis system according to an embodiment of the present teachings.

FIGS. 1 and 2 schematically depict a dialysis system 100 in which a VND detection system 102 according to an embodiment of the present teachings for the detection of venous needle dislodgement (VND) is incorporated.

The depicted hemodialysis dialysis system 100 includes a dialyzer 103 that receives arterial blood via an arterial line 109, which in turn receives the blood through an arterial access point 110 (e.g., arteriovenous (AV) fistula). A blood pump 108a facilitates the circulation of the blood through the dialysis system. A blood thinner, e.g., heparin, may be introduced into the blood flow via a heparin pump 108 prior to its introduction into the dialyzer 103. The dialyzer 103 filters the blood and the filtered blood is returned to the patient via a venous return line 105 that is coupled to a patient's vein via a venous access point 107 (e.g., arteriovenous (AV) fistula), which includes a venous needle 107a that is inserted into the patient circulatory system. An air detector/air trap 111 may be coupled to the venous return line to prevent air bubbles, if any, in the flowing blood from being introduced into the patient.

By way of example, the dialyzer 103 can include thousands of tiny porous tubes, where the blood flows inside the tubes and a dialysate solution flows outside the tubes. The pores in the tubes allow the waste and excess fluids to pass from the blood to the dialysate. The used dialysate is discarded via an outlet port of the dialyzer and fresh dialysate is introduced into the dialyzer from a reservoir via an inlet port of the dialyzer.

Figure 2A:
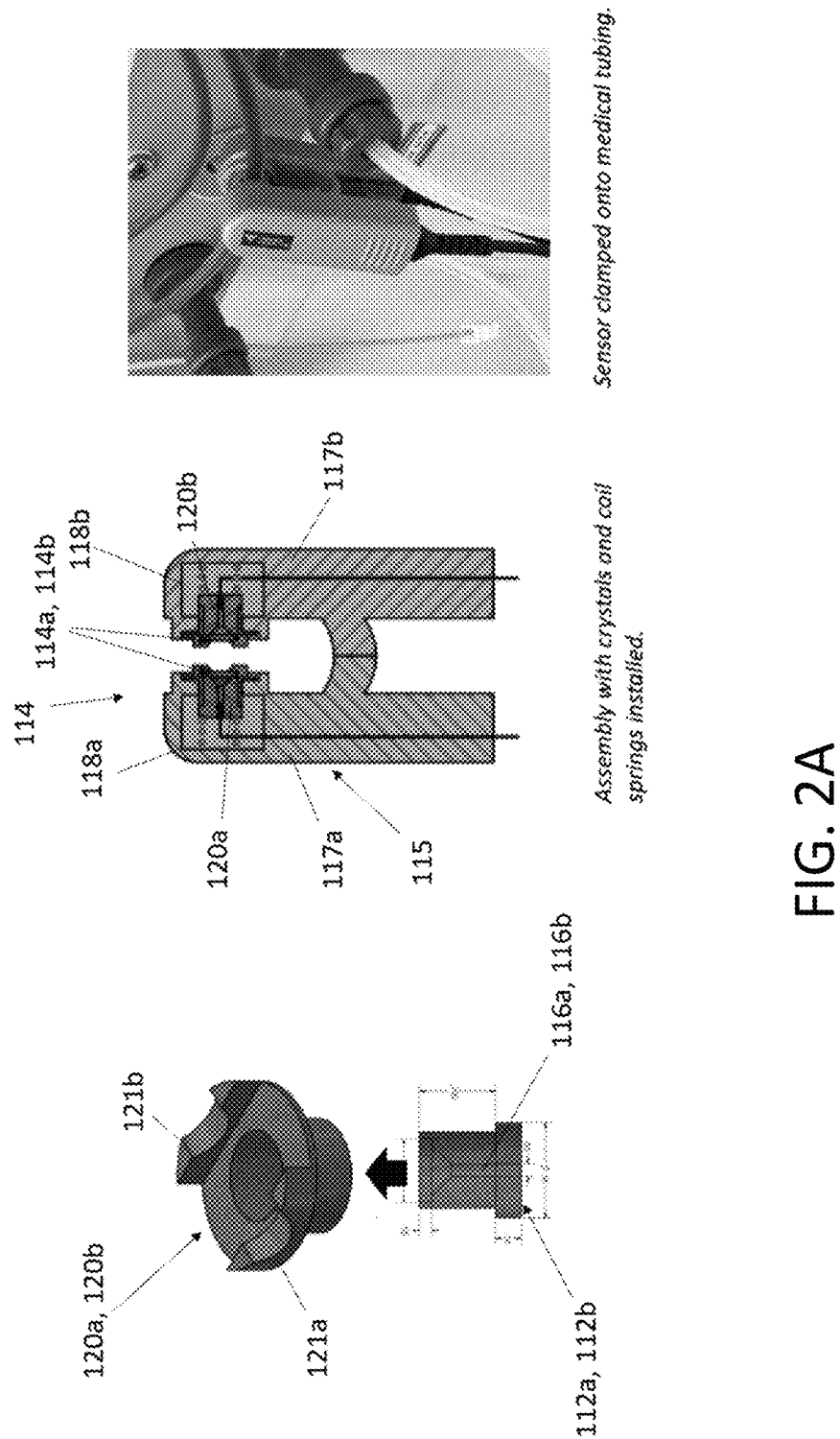
FIG. 2A shows a clamp in two arms of which the transmit and receive acoustic transducers are housed, where the clamp is employed for releasable coupling of the venous return line to the acoustic transducers.
Figure 2B:
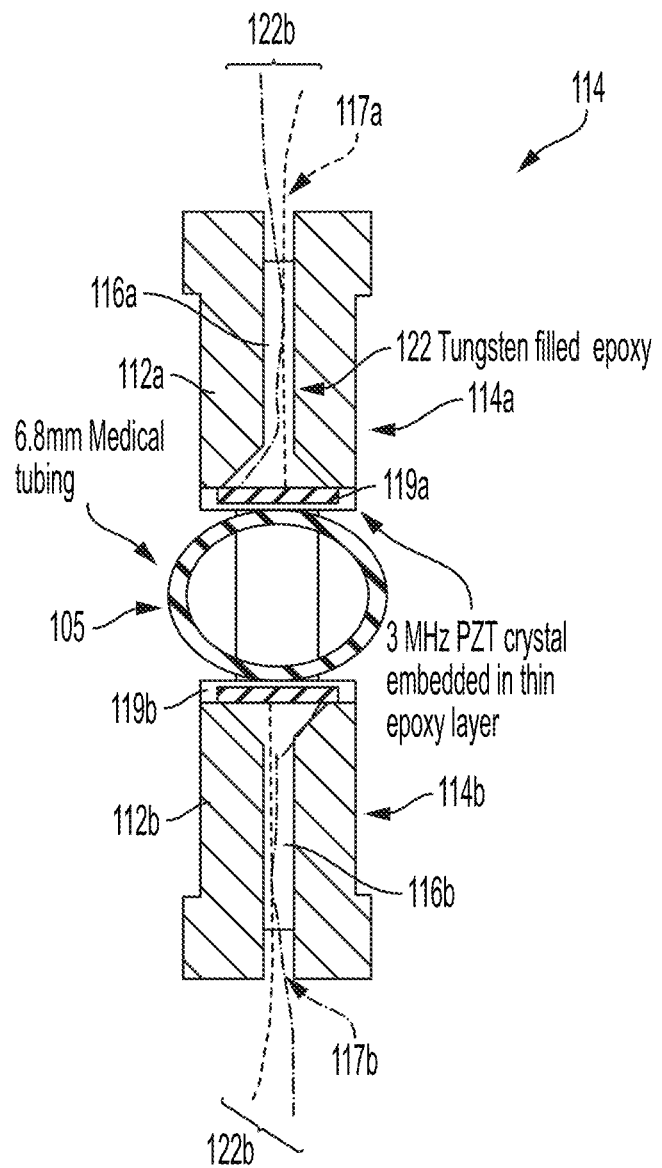
FIG. 2B schematically depicts an acoustic sensor according to an embodiment of the present teachings.

With continued reference to FIG. 1 as well as FIGS. 2A and 2B, in this embodiment, the VND detection system 102 includes an acoustic sensor 114 having an acoustic transmit unit 114a and an acoustic receiver unit 114b (e.g., as illustrated in FIG. 2B), which may be coupled (e.g., releasably) via a clamp 115 to a portion of the venous return line 105. A variety of acoustic transmit and receive units can be employed. For example, on non-limiting examples is an ultrasonic transducer marketed by Ultran under model number PT25-4-X which may be employed. The clamp 115 of acoustic unit 114 may include two arms 117a and 117b that are spring-biased relative to one another to allow releasably holding a portion of the venous blood line 105 between the tips of the two arms.

The tips of the two arms 117a/117b of the clamp 115 may include recesses 118a and 118b for receiving two mounting elements 120a/120b, where each of the mounting elements 120a/120b is in turn configured to receive one of the acoustic transducer units 114a and 114b of the acoustic sensor 114, as discussed in more detail below. Further, each mounting element 120a/120b includes a pair of projections (such as projections 121a/121b) that can come into contact with a respective pair of projections of the other plastic element upon securing a portion of the venous return line between the two arms of the clamp.

With reference to FIGS. 2A and 2B, each acoustic transducer unit 114a/114b includes a housing 112a/112b configured to be positioned within the central opening of mounting elements 120a/120b (e.g., as shown in FIG. 2A). Housings 112a/112b may be formed in this embodiment of a suitable plastic material (e.g., polydimethylsiloxane (PDMS)) and may include a lumen 116a/116b, which may extend from a proximal end of the housing to its distal end and which exhibits a widening taper that terminates at the distal surface of the housing. Each of the housings 112a/112b accommodates a piezoelectric transducer 119a/119b for transmitting or receiving an acoustic signal.

A plurality of conductive elements 122a/122b extend through the lumens of the housings and are electrically coupled to the transducers 114a/114b to supply electrical power to the transmit transducer unit 114a and to receive one or more detection signals generated by the receive transducer unit 114b and transmit the detection signal(s) to a signal processing/analysis module, as discussed in more detail below. In this embodiment, the lumens of the two transducer housings are at least partially filled with a tungsten epoxy 122 for the purpose of broadening the frequency response of the transducers.

Each acoustic transducer unit 114a/114b can be removably positioned in a respective recess of one of the mounting elements 120a/120b. The acoustic transducer units can be spring-loaded to allow flexibility in their contact with the portion of the venous line held between the tips of the clamp 115. For example, the pulsation of the blood flowing through the venous line can cause some degree of expansion and contraction of the venous line. A flexible contact between the transmit and receive transducer units 114a/114b and the venous line (i.e., a contact that is not too rigid and hence allows the radial expansion and contraction of the venous line to occur) allows such radial oscillations of the venous line to contribute to a phase shift between the transmit and the receive acoustic signals, as discussed in more detail below.

Figure 3A:
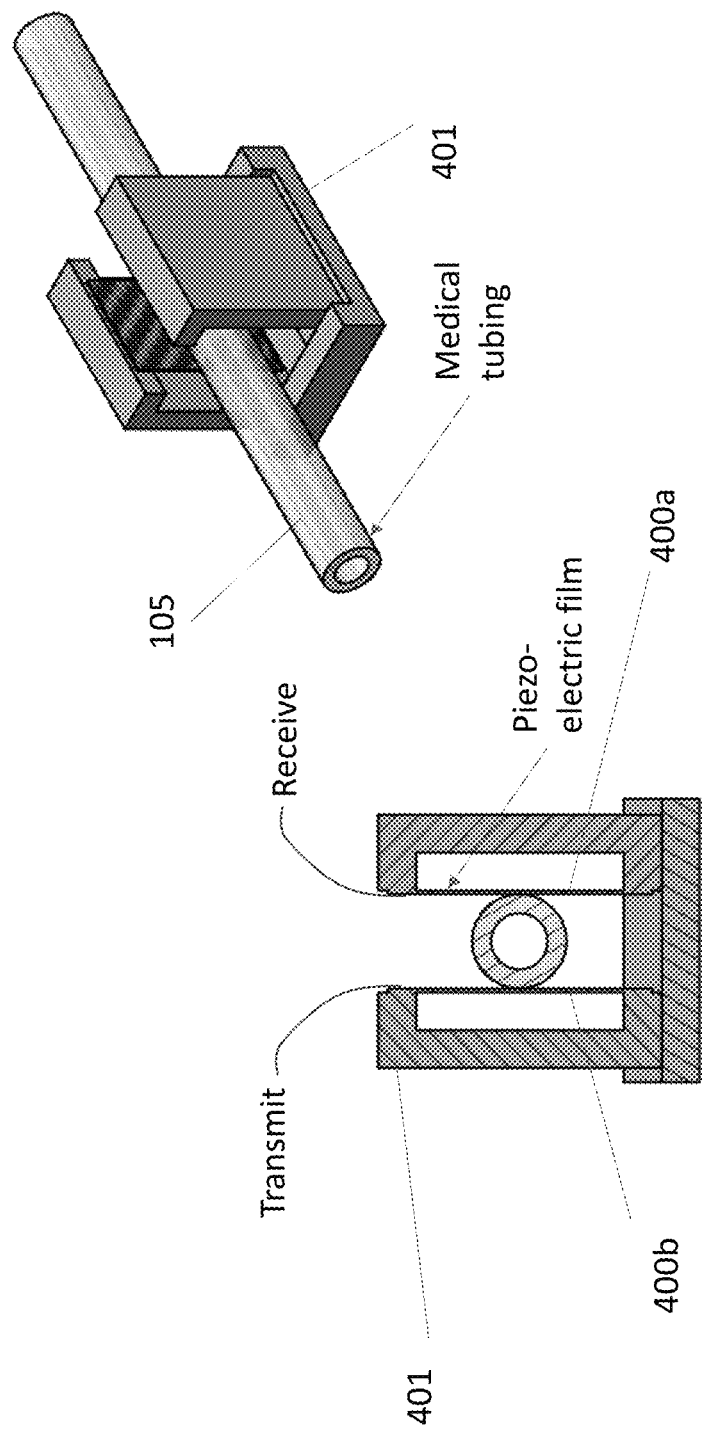
FIG. 3A schematically depicts an acoustic sensor according to an embodiment in which piezoelectric films are employed for generating and detecting acoustic waves.

In some embodiments, piezoelectric films can be employed for generating and/or receiving the acoustic signals. By way of example, FIG. 3A schematically depicts such an embodiment in which two piezoelectric films 400a/400b are disposed on opposed sides of a portion of the venous return line 105. A clamp 401 is employed to maintain the piezoelectric films 400a/400b in position relative to the venous return line 105. In this embodiment, the piezoelectric film 400a is employed to generate an acoustic signal for transmission through the venous line in a direction that is substantially perpendicular to the direction of fluid flow, and the piezoelectric film 400b is employed to receive at least a portion of the transmitted signal and generate a detection signal. For example, an oscillating voltage applied to the piezoelectric film 400a can cause vibration of that film to generate an acoustic signal for transmission into the lumen of the line. The acoustic waves passing through the medium flowing through the line can cause vibratory motion of the piezoelectric film 400b, which in turn results in the generation of an electrical signal.

Referring again to FIG. 1, a transmit/receive unit 200 operates under the control of a control and signal processing unit 201 to control the acoustic transmit and receive transducers 114a/114b. In particular, the control and signal processing unit 201 can operate the acoustic transmit unit to transmit a continuous-wave (CW) acoustic signal across the diameter of the venous line 105 and the acoustic receive unit to detect at least a portion of the transmitted acoustic signal after its passage through the venous line walls and the flowing blood. In this manner, a standing-wave acoustic resonance can be established within the inside diameter of the venous line between the acoustic transmit and receive units.

The frequency of the acoustic signal can be selected to facilitate establishment of the standing-wave acoustic resonance within a transverse dimension of the venous line. A standing wave is established in a fluid when an integral number of half wavelength of the acoustic wave fits within the fluid path. By way of example, the frequency of the acoustic wave can be in a range of about 1 to about 20 MHz, e.g., in a range of about 5 MHz to about 10 MHz, though other frequencies can also be employed. The choice of the frequency is generally based on the sound transmission properties of the tube material and not a limitation of the present teachings. For example, in this embodiment, the frequency of the acoustic wave is around 3 MHz, though other frequencies can also be used. This frequency is chosen based on the maximum amplitude of the received signal that indicates a resonance condition and it depends on the tube diameter and the fluid sound speed. As discussed in more detail, in some embodiments, the frequency of the applied acoustic signal can be swept and the detected phase signal can be monitored in order to identify an optimal frequency (i.e., a frequency leading to the establishment of a resonant acoustic wave) for application to the acoustic sensor.

As discussed in more detail below, a phase difference between the transmit and receive signals changes in response to venous pulsations and/or other variations in the fluid dynamics of the flow.

As shown in FIG. 1, a detection signal generated by the acoustic transducer receiver unit 114b is received by a signal processing module 202. The signal processing module 202 includes a low-noise amplifier (LNA) 204 that amplifies the received signal. A phase detector 205 receives a portion of the transmit signal as well as the amplified receive signal and compares the phases of the two signals to generate a phase difference signal. The phase difference signal is filtered by a low pass frequency filter 207, which has, in this embodiment, a cut-off frequency of about 100 Hz, and is amplified by an amplifier 209 prior to its transmission to the transmit/receive unit 200, which is in communication with the control and signal processing unit 201.

With continued reference to FIG. 1, the transmit/receive unit 200 includes an ADC (analog-to-digital converter) module that receives the amplified phase signal and digitizes that signal. The ADC is in communication with a FPGA (field programmable gate array) that receives a reference signal from a crystal oscillator, provides a sampling clock for sampling the digitized phase signal, and transmits the sampled digitized phase signal, via a USB control module, to a communication interface of the control and signal processing unit 201. The control and signal processing unit 201 can be configured to operate on the received acoustic signal, e.g., in a manner discussed herein, to detect a change in the fluid dynamics of the flowing fluid, e.g., a partial or complete VND event.

In addition to the communication interface, the control and signal processing unit 201 includes a processor, a memory module as well as a display and a keypad. By way of example, the processor can be a general and/or special purpose microprocessor, such as an application-specific instruction set processor, graphics processing unit, physics processing unit, digital signal processor, image processor, coprocessor, floating-point processor, network processor, and/or any other suitable processor that can be used in a digital computing circuitry. Alternatively or additionally, the processor can comprise at least one multi-core processor and a front-end processor. By way of example, in some embodiments, the memory module can include one or more permanent memory units and one or more random access memory (RAM) units. By way of example, the permanent memory units can be magnetic disks (e.g., internal or removable disks), magneto-optical disks, one or more of a semiconductor memory device (e.g., EPROM or EEPROM), flash memory, CD-ROM, and/or DVD-ROM disks.

Instructions and data for operating various components of the system, such as the acoustic transducers, the blood pump, as well as analysis of the detected acoustic signals according to the present teachings can be stored in the permanent memory and can be transferred onto the RAM during execution.

A communication bus allows communication among various components of the control and signal processing unit 201. In some embodiments, instructions for analysis of the received phase signal can be stored in the memory module. The processor can execute these instructions to analyze the received phase signal, i.e., the phase difference data. As discussed in more detail below, the analysis of the phase difference data may result in the detection of a deviation from an expected signature. In some embodiments, the control and signal processing unit 201 can be configured to generate an alarm in response to the detection of such a deviation of the phase signal. In some embodiments, the control and signal processing unit 201 can be configured to communicate with the blood pump 108a to adjust the pump's speed in response to the detection of a deviation of the phase signal from an expected phase signature.

More specifically, in this embodiment, the control and signal processing unit 201 can be configured to operate on the phase difference signal to determine whether a VND event has occurred. In particular, the control and signal processing unit 201 can be configured to compare the measured phase difference signal, e.g., the temporal variation of the phase difference signal, with an expected phase signal associated with an expected blood flow signature to identify, e.g., disruption and/or abnormal flow, if any, associated with the blood flowing through the venous line. More specifically, in this embodiment, the expected phase signature is a signature associated with the heartbeats of the patient undergoing dialysis. In other words, when the venous needle is securely positioned within the patient's vein, the patient's heartbeats can generate a characteristic pulsation in the venous line, which can be detected as a heartbeat phase difference signature. Such a heartbeat phase signature can be monitored to identify a venous needle dislodgement (e.g., a partial or a substantially complete dislodgement). For example, a venous needle dislodgement can result in a substantial disappearance of the unique heartbeat phase signature.

With continued reference to FIG. 1, the control and processing unit 201 is also configured to control the operation of the transmit/receive unit, e.g., to instruct the transmit/receive unit to apply a desired acoustic frequency to the VND acoustic sensor 114. For example, in this embodiment, the control and processing unit 201 can be configured to send control signals to a waveform generator (AWG), which is incorporated in the FPGA, to generate a digital frequency signal at a desired frequency for application to the acoustic sensor 114.

A digital-to-analog converter (DAC) converts the digital frequency signal to an analog signal, which can be stored in a buffer for application to the acoustic sensor 114. A portion of the signal can provide a reference signal to the phase detector for determining a phase difference between the transmit and receive signals.

In some embodiments, the control and processing unit 201 sweeps the acoustic frequency applied to the acoustic sensor 114 over a frequency range to determine an optimal acoustic frequency for application to the acoustic sensor, e.g., a resonant acoustic frequency.

Figure 10D:
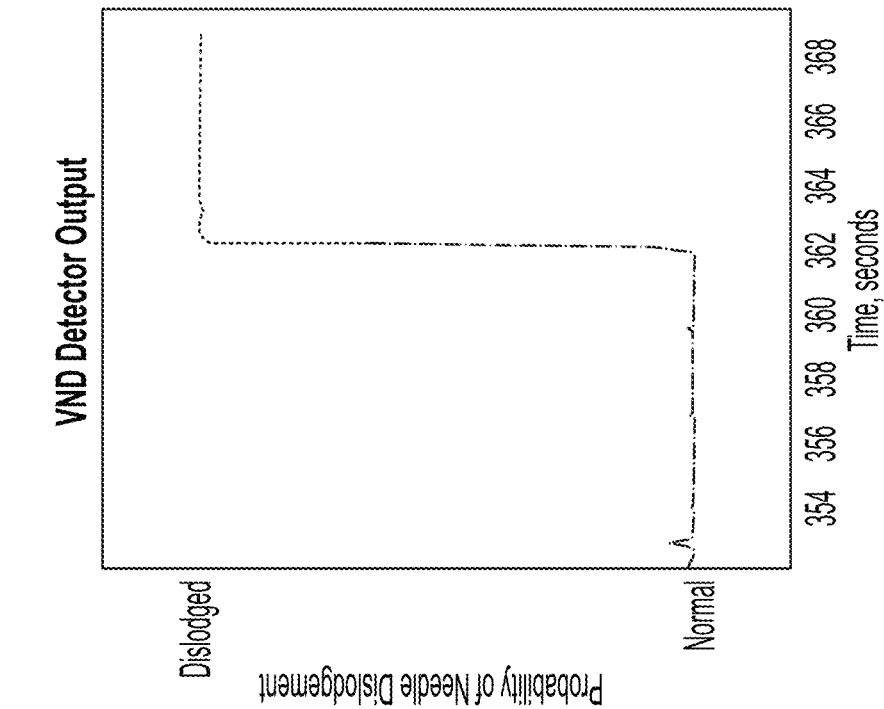
FIG. 10D shows a probability for a VND event derived based on the phase signal shown in FIG. 10C.
Figure 10C:
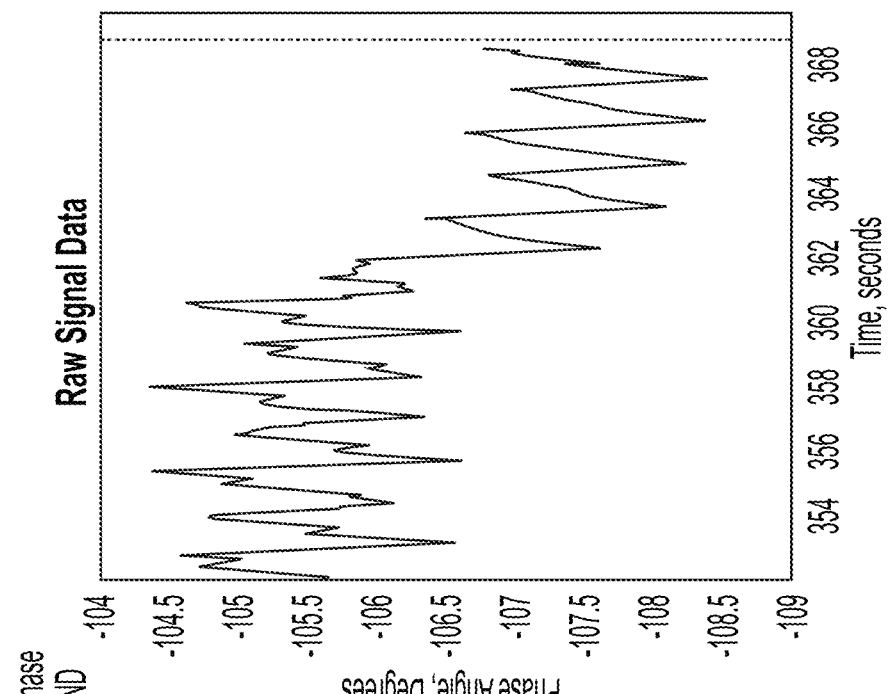
FIG. 10C shows a simulated phase signal indicative of a VND event.

As noted above, the control and processing unit 201 receives the phase difference signal and monitors that signal for indication of a deviation of the phase signal from an expected phase signature. In some embodiments, the control and processing unit 201 can be configured to apply a moving FFT window to the phase signal to analyze the signal for the detection of a phase deviation from an expected phase signal. By way of example, FIG. 10A shows a simulated phase signal corresponding to normal operation. FIG. 10B shows a probability for a VND event derived from the phase signal. FIG. 10C shows a simulated phase signal indicative of a VND event, and FIG. 10D shows a probability for a VND event derived from the phase signal shown in FIG. 10C. In this example, a number of independent features characterizing the phase signature was used in a probabilistic classifier algorithm to determine the likelihood that a VND event has occurred. This approach has been shown to provide a fast step change response, e.g., as shown in FIG. 10D, while minimizing the occurrence of false alarms.

In some embodiments, a change in the monitored phase signal relative to an expected phase signature can be employed to detect one or more blood clots in the fluid flow. For example, one or more blood clots can be detected via the detection of a phase shift and/or a change in the amplitude of the receive signal.

In some embodiments, the methods and systems disclosed in U.S. Pat. No. 7,228,740 (herein referred to as "the '740 patent"), which is herein incorporated by reference, can be employed as informed by the present teachings to measure a phase difference between the transmit and the receive acoustic signals and to analyze the measured phase signal to obtain information about changes in the composition of the blood. Further, the methods and systems disclosed in the '740 patent can be employed to provide a sweep of the acoustic frequency, measure the phase difference signal as a function of frequency, and analyze the frequency dependence of the measured phase difference signal to obtain compositional information.

The above embodiment is hardware-based. As discussed in more detail below, phase detection can be performed via software operations performed on digitized transmit and receive signals, as discussed in more detail below.

Figure 3B:
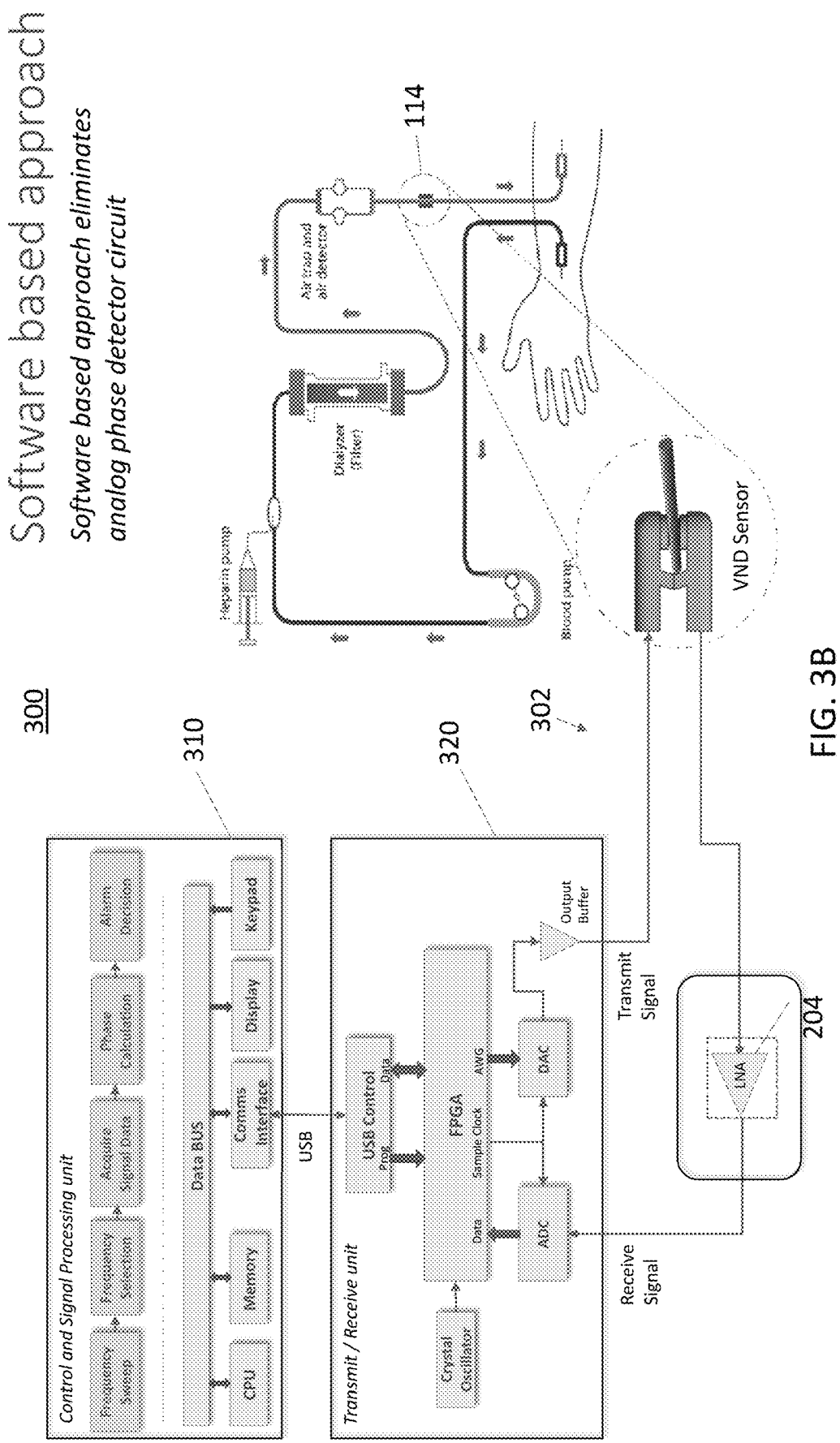
FIG. 3B shows a schematic view of another embodiment of a venous line dislodgement system according to the present teachings incorporated in a dialysis system in which a software approach is employed for determining the phase difference and for data analysis.

More specifically, FIG. 3B schematically depicts a dialysis system 300 in which a VND detection system 302 according to another embodiment of the present teachings is incorporated. Similar to the dialysis system 100 discussed above, the acoustic sensor 114 may be coupled (e.g., releasably) to the venous return line of the dialysis system. In this embodiment, the transmit/receive unit 320 operating under the control of the control and signal processing unit 310 actuates the acoustic transmit unit 114a to launch an acoustic wave across the diameter of the venous return line and receives detection signals generated by the receive acoustic unit 114b after the amplification of the detection signals by the low-noise amplifier 204.

In this embodiment, the detection of a phase difference between the transmit and receive acoustic signals is performed by a software module residing on the control and signal processing unit 310. For example, the amplified high frequency acoustic signal output by the low-noise amplifier 204 is received by the transmit/receive unit 320, which in turn sends a digitized version of the acoustic signal to control and processing unit 310. Instructions, such as those discussed below, stored on the control and processing unit 310 can then be employed to determine a phase difference between the transmit and the receive acoustic signals.

By way of example, the following procedure can be employed to determine and analyze the phase signal.

The phase of the signal is given by the following equation:

$$\phi = \operatorname{atan}\left(\frac{Q}{I}\right) \qquad \text{Equation (1)}$$

where I is the in-Phase component of the signal, typically referred to as the real component, and Q is typically referred to as the quadrature component or the imaginary component of the signal. According to the above equation, to calculate the phase angle, one needs to calculate I and Q. The section below outlines the steps needed to calculate I and Q.

I and Q Generation:

The procedure for calculating I and Q is shown in the steps below. In the following discussion, Rx is the signal measured from the receive transducer and Tx is the directly measured transmit signal.

1. The first step in generating I and Q is to create an in-phase and quadrature version of the transmit signal. This can be done by applying the Hilbert transform to the measured transmit signal. This creates a complex signal, in which the real component of the transformed signal is the in-phase component (which is just a replica of the original transmit signal) and the imaginary component is a 90-degree phase shifted version of the original transmit signal (also known as the quadrature component).
2. The next step is to mix the in-phase and quadrature components with the received signal (Rx). By way of example, mixing can be done by applying a point-by-point multiplication of the two signals.
3. After mixing the signals, a low pass filter (lpf) can be applied to the mixed signal.
4. Subsequently, in some embodiments, the data can be cropped, e.g., keeping the middle 80% of the low pass filtered signal. This can reduce the influence of end-effects which are generated by low pass filtering step.
5. Finally, the mean of the cropped data can be determined, which yields I and Q, respectively.

Figure 3C:
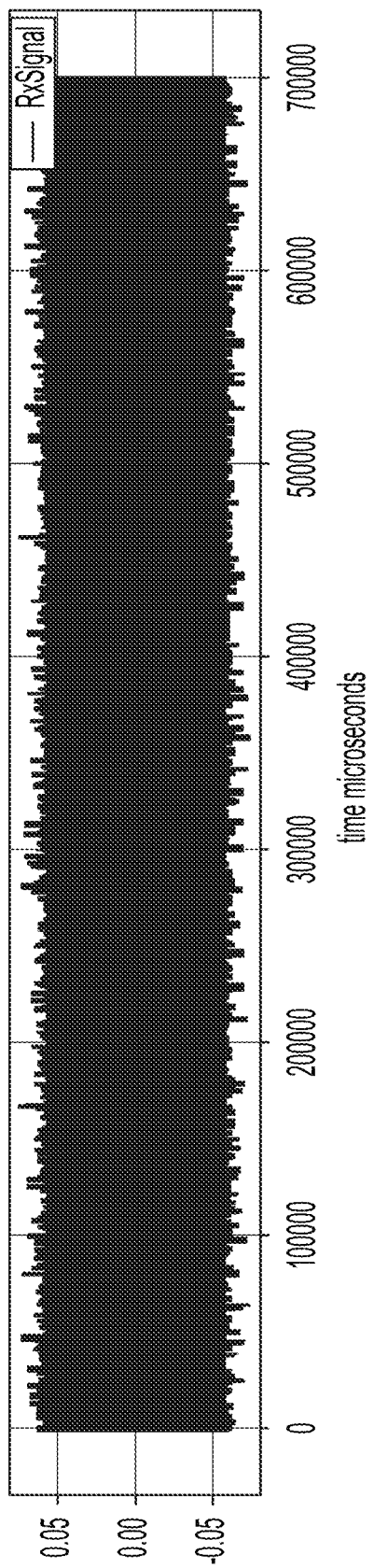
FIG. 3C presents a detected acoustic signal obtained by using a simulated circuit, which is described in the Examples section below.
Figure 3D:
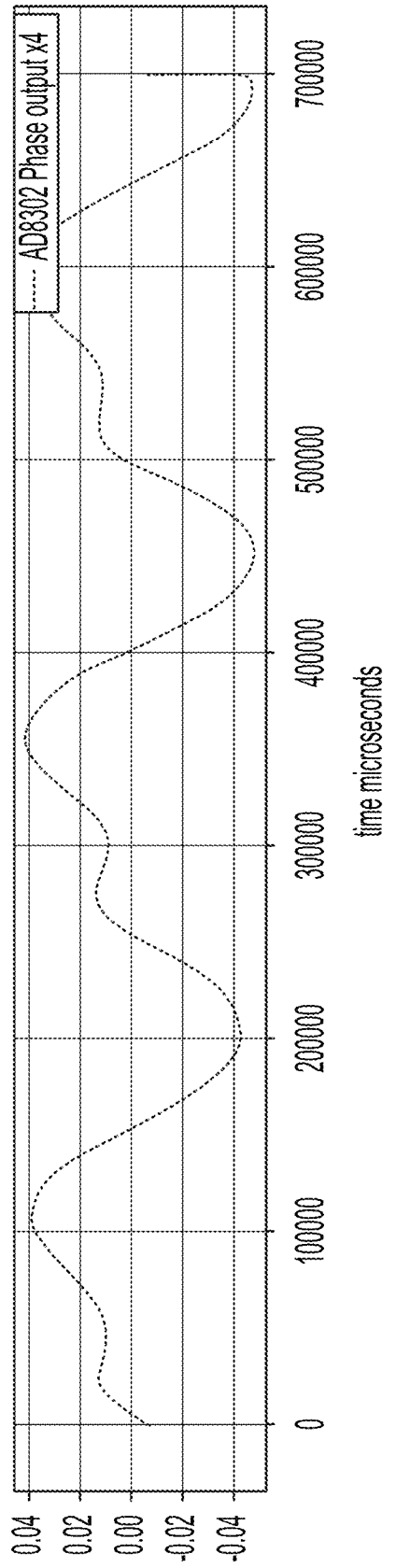
FIG. 3D shows a phase difference signal associated with the acoustic signal in FIG. 3C, where the phase difference signal is determined using analog methods.
Figure 3E:
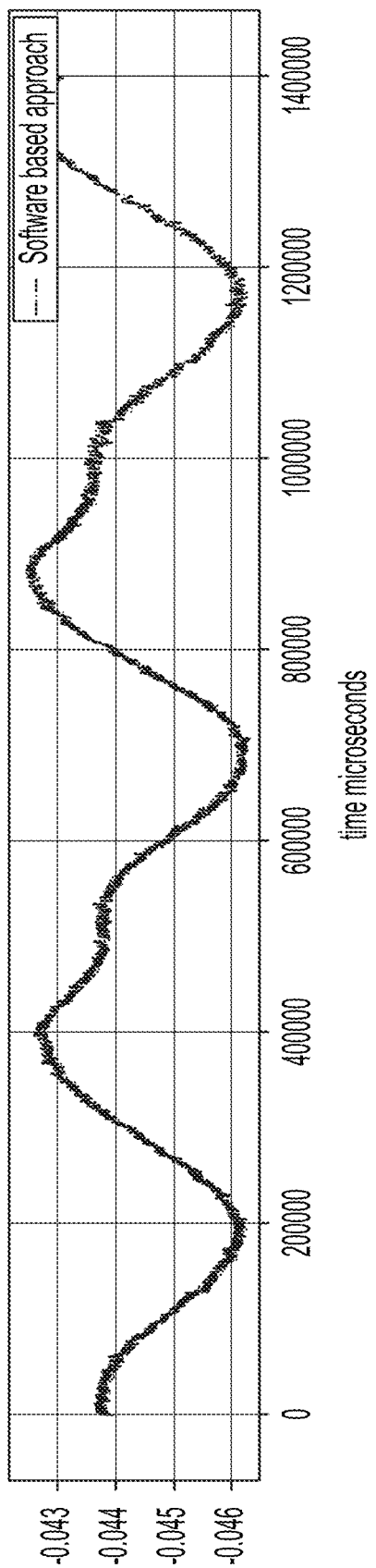
FIG. 3E shows a phase difference signal associated with the acoustic signal in FIG. 3C, where the phase difference signal is determined using a software approach.

By way of illustration, FIG. 3C presents an acoustic receive signal obtained by using a simulated circuit discussed below in the Examples section. The presented acoustic receive signal has a frequency of 3 MHz and a duration of 0.7 seconds. FIG. 3D shows a phase difference signal associated with the acoustic signal presented in FIG. 3C (i.e., a phase difference between the transmit signal and the receive signal), where the phase difference signal was obtained by using analog circuitry (AD8302 chip). FIG. 3E presents a phase difference signal associated with the acoustic signal presented in FIG. 3C, where the phase difference signal was generated using software.

As discussed further below, upon the detection of a partial or complete VND, certain measures can be undertaken. For example, with reference to FIG. 1, the control and signal processing unit 201 can be configured to turn off the pump 108a to slow down the blood loss.

In some embodiments, upon the detection of a VND, the control and signal processing unit 201 is configured to delay taking any action for a pre-defined period of time, e.g., a time period in the range of about 5 to about 10 seconds, and continue monitoring the phase difference signal to ensure that a VND event has in fact occurred. Such an approach can ameliorate the occurrence of false positives.

In some embodiments, in response to the detection of a phase variation indicative of a change in the fluid dynamics of the flow, the control and signal processing unit 201 can be configured to adjust the speed of the blood pump 108a. For example, the speed of the blood pump 108a can be reduced and the phase signal can be monitored until no air bubbles are detected in the flow.

Figure 4:
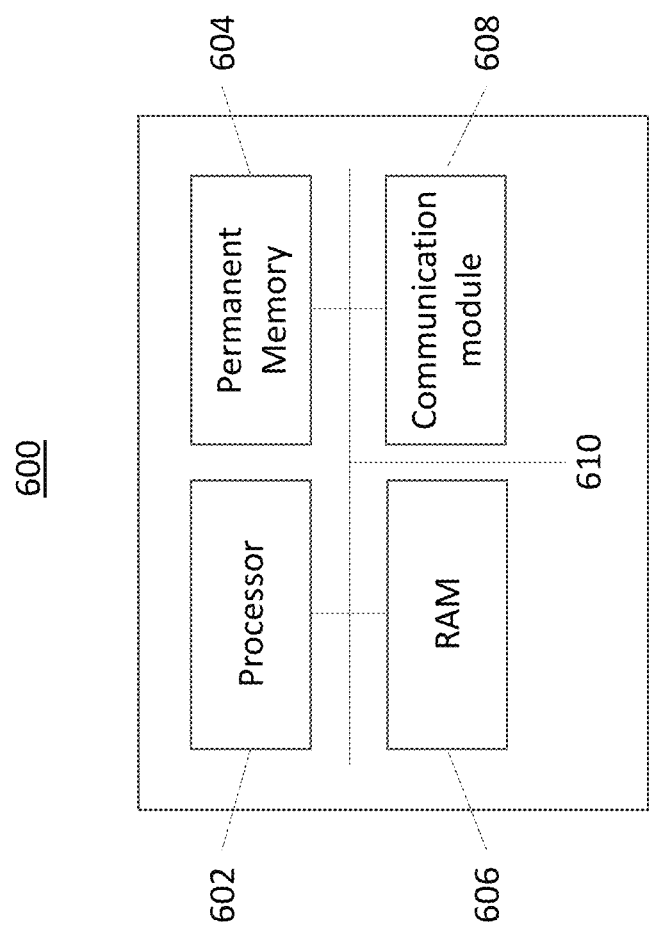
FIG. 4 schematically depicts a hardware platform for a control and signal processing unit according to the present teachings.

The control and signal processing unit 201 can be implemented using hardware, software and/or firmware in a manner known in the art, as informed by the present teachings. By way of example, FIG. 4 schematically depicts a hardware platform 600 that includes, among other components, a processor 602, a permanent memory 604, a random access memory (RAM) 606, and a communications module (WIFI or Bluetooth) 608, and a communications bus 610 for connecting the processor 602 to these components.

As noted above, in some embodiments, an acoustic sensor as described herein may be configured to be positioned at the arterial or venous drip chambers which are found on available HD machines. The diameter of these chambers may range, for example, from about 18 mm to about 30 mm.

The following Examples are provided for further elucidation of various aspects of the present teachings. The Examples are provided for illustrative purposes and are not intended to necessarily indicate optimal ways of practicing the present teachings and/or optimal results that can be obtained.

Example 1

A simulated venous pulse (Fistula) connected to the output of a blood pump (the pump of Fresenius dialysis machine, Model: 2008T, which is herein referred to as "Fresenius blood pump") via a hemodialysis needle was employed to detect simulated venous pulses above the "noise" generated by the blood pump.

Figure 5A:
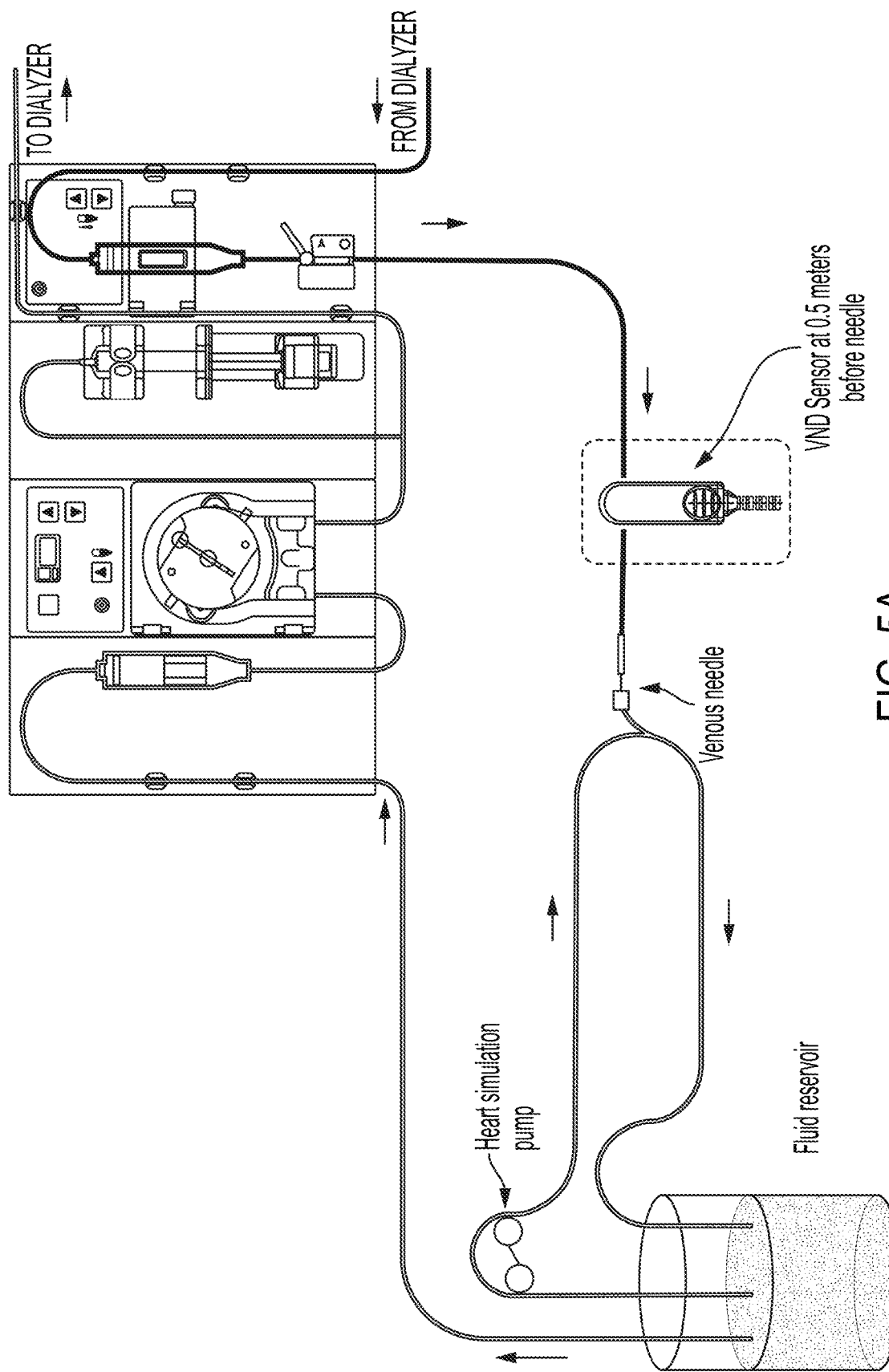
FIG. 5A schematically depicts a simulation circuit employed to simulate the functionality of a system according to an embodiment of the present teachings for detecting VND in an extra-corporeal circuit of a dialysis system.

FIG. 5A shows the simulated circuit that was employed for detecting the venous pulse using a phase detection system and method according to an embodiment of the present teachings The figure shows the hydraulics circuit and location of the VND sensor and dialysis needle insertion point relative to the heart pulse simulation pump and Fresenius blood pump.

A Fresenius medical tubing for the model 2008T dialysis machine set was used, including the specified dialyzer part number 16LU04016. The VND system was evaluated with the blood pump set to 100-275 ml/min and with the VND sensor located at 0.5 m before the venous needle.

The venous or heart pulsation (fistula) was simulated using a small peristaltic pump into which the venous needle is inserted.

Figure 5B:
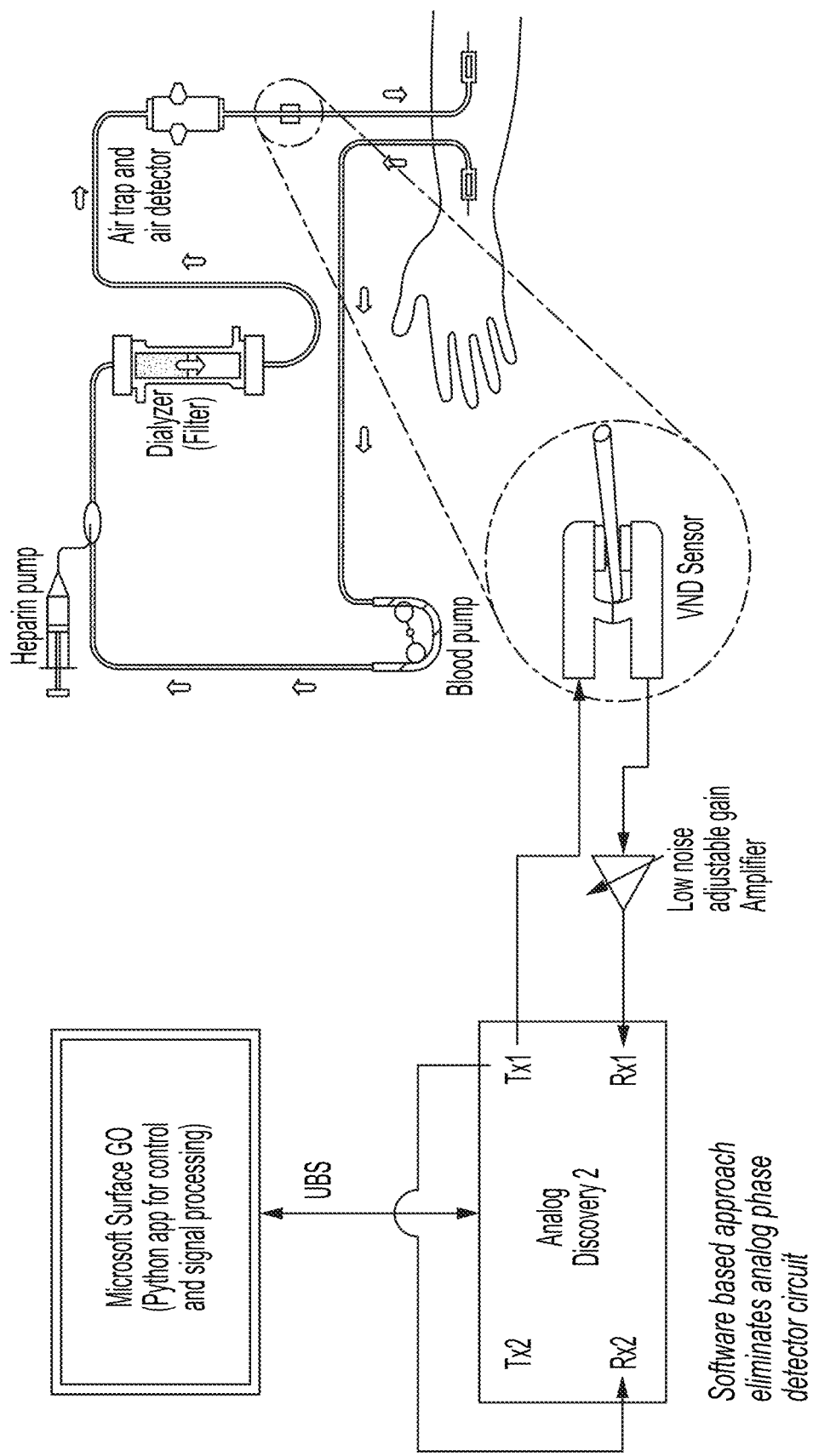
FIG. 5B schematically depicts hardware components employed in the simulation circuit depicted in FIG. 5A.
Figure 6A:
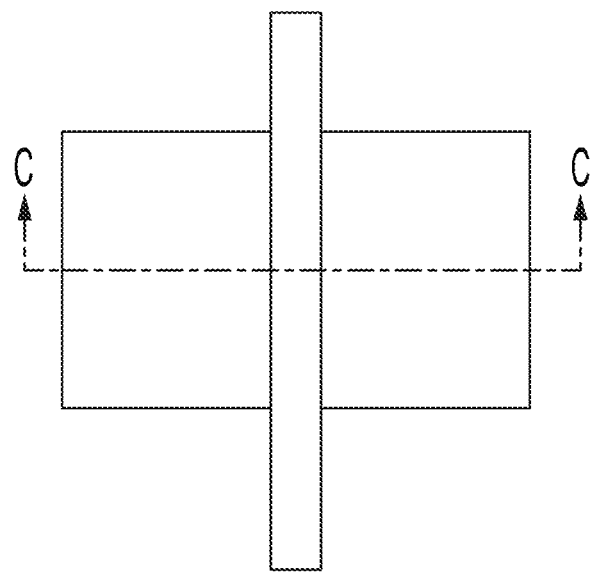
FIGS. 6A and 6B depict various schematic views of a clamp employed in the simulation circuit of FIG. 5A for coupling an acoustic sensor according to the present teachings to a portion of an extra-corporeal line of the simulation circuit.
Figure 6B:
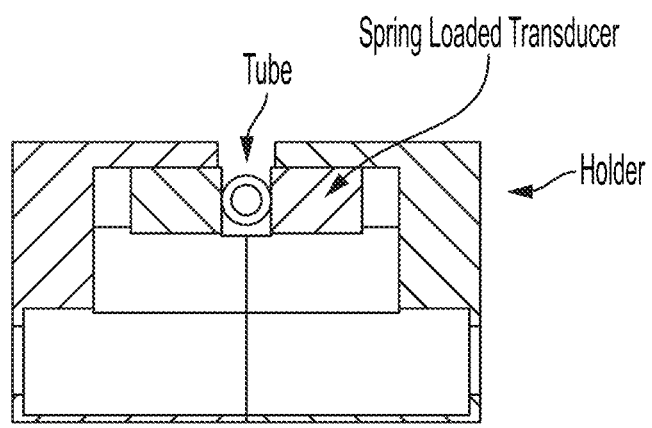

The hardware used to transmit and receive signals to and from the VND sensor, as well as process the signals for accurate phase detection, is shown in FIG. 5B.

A dual-channel Analog Discovery 2 device was employed to transmit a continuous wave signal (Tx1) into one piezo element in the VND sensor while the signal from the second piezo element was received via Rx1.

To ensure a precise phase difference measurement, the same Tx1 transmit signal was also measured using the second input channel (Rx2) on the Analog Discovery 2 device.

An application software written in Python® programming language operating on a tablet computer was used to control the Analog Discovery 2 device, process the received signals, in a manner discussed above, and log the raw processed data.

The following procedure was used to obtain test results:

1. Equipment Setup:

1.1 Install 6.5 mm medical tubing and dialyzer into the Fresenius 2008T dialysis machine. Using similar medical tubing and specified peristaltic pump, form the heart simulator circuit as shown in FIG. 5A.

1.2 Install the VND sensor onto the venous line approximately 0.5 m before the venous needle as shown in FIG. 5A. Use petroleum jelly to acoustically couple the sensor to the tubing.

1.3 Connect BNC connectors to the VND sensor.

1.4 Fill the blood reservoir with red dyed water.

1.5 Turn on the Fresenius dialysis machine and enter "Service" mode, then select "Maintenance" and "Art Pump". This allow manual control of the blood pump flow rate. Set the pump rate to 100-275 ml/min then turn the pump off.

1.6 Fill the venous simulation line and dialysis line by simultaneously running both pumps.

1.7 Launch the VND application and START the measurement.

1.8 Set up two USB webcams to record the tablet PC screen and the dialysis needle insertion area. Start the recording before executing the test steps below.

2. Test steps 2.1 Turn on the heart simulation pump to the lowest setting (3.5V) and verify that pump pulsations are observed by viewing the phase output signal on the VND app.

2.2 Carefully remove the dialysis needle from the pulse simulation line over a suitable catch basin. Verify that the phase output signal is now flat (i.e. no pulsations).

2.3 Reinsert the dialysis needle and verify that pump pulsations are once again observed by viewing the phase output signal on the VND app.

2.4 With the venous pulse simulation pump still running, turn on the Fresenius blood pump.

2.5 Carefully remove the dialysis needle from the pulse simulation line. Verify that the phase output signal is noticeably reduced in amplitude, showing only the smaller pulsations from the blood pump.

2.6 Very slowly reinsert the dialysis needle to demonstrate that the venous pulsations are observed only after the needle is fully inserted and not leaking.

2.7 Set the blood pump rate to 500 ml/min then remove the dialysis needle from the pulse simulation line. Verify that the phase output signal shows a noticeable change in the frequency content or experiences a significant phase shift.

2.8 Reinsert the dialysis needle to demonstrate that the venous pulsations are again observed only after the needle is fully inserted and not leaking, and that the average phase value returns to the previous state.

Figure 7:
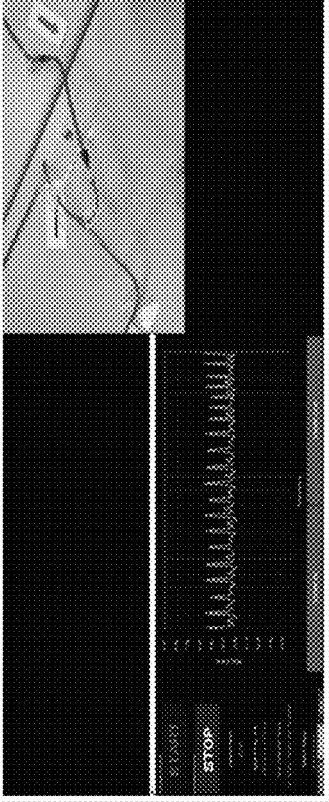
FIGS. 7, 8, and 9 present oscilloscope traces indicative of the phase signals at various stages of a test for simulating the detection of a VND event in an extra-corporeal dialysis system.
Figure 8:
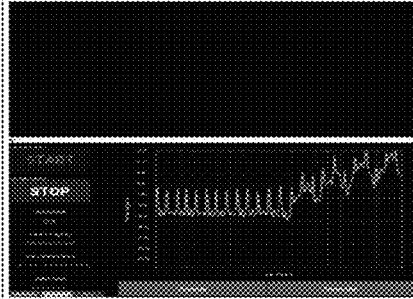
Figure 9:
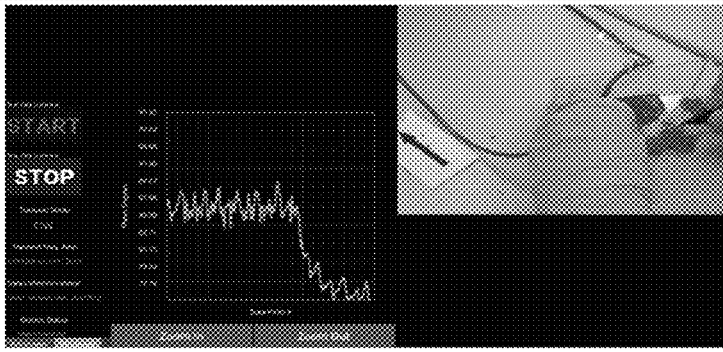

FIGS. 7, 8, and 9 present oscilloscope traces of the phase detection signals associated with the test steps noted above.

With reference to FIG. 7, Panel A shows the observed phase signal upon turning on the venous pump. Panel B shows the phase signal upon removal of the dialysis needle with the venous pump running, exhibiting a substantial disappearance of the characteristic signature of the phase signal observed in Panel A. And Panel C shows the phase signal upon re-insertion of the dialysis needle, showing the re-appearance of the characteristic signature of the phase signal.

With reference to FIG. 8, Panel A shows the observed phase signal when the Fresenius blood pump was turned on. Panel B shows the phase signal upon removal of the dialysis needle with both pumps running, exhibiting a substantial disappearance of the characteristic signature of the phase signal observed in Panel A. And Panel C shows the phase signal after a slow re-insertion of the dialysis needle, exhibiting a gradual re-appearance of the characteristic phase signature observed in Panel A.

With reference to FIG. 9, Panel A shows the phase signal when the blood pump rate was set at 500 milliliters/min followed by the removal of the dialysis needle with the venous pump still running, exhibiting a significant change in the phase signal due to the removal of the dialysis needle. Panel B shows the phase signal upon a slow re-insertion of the dialysis needle, exhibiting a gradual return of the phase signal to the characteristic phase signal observed in Panel A.

The above results demonstrate that the tests were successfully performed and they show the feasibility and high sensitivity of an embodiment of a system and a method according to the present teachings for VND detection, even when the blood pump was operating at a flow rate of 500 ml/min.

Those having ordinary skill in the art will appreciate that various changes can be made to the above embodiments in view of the present teachings without departing from the scope of the claimed subject matter.

Example 2

A clinical study was conducted with a prototype VND sensor system according to the present teachings. The clinical study was performed on ten patients, and two data collections per each patient, i.e., a total of 20 data sets, were collected. Of the 10 patients, 9 patients had fistula access and 1 patient used a catheter access.

Throughout the clinical study, the system demonstrated consistent measurements between patients, and signals attributed to the dialysis machine were consistent and repeatable. Many of the signatures measured correlated with the events noted in the treatment log recorded with each data collection. Further, the testing results indicated that there were no significant effects attributed to patient movement.

Examination of the data signatures collected during the clinical study indicate that the VND sensor system according to the present teachings can detect various signals that are generated by the normal operation of the dialysis machine. Based on the signatures measured, the measurement techniques according to the present teachings have been demonstrated to be capable of distinguishing the VND events from various other signatures occurring from the operation of the dialysis procedure.

For the clinical study, a VND detection sensor was retrofitted into Model 2008T dialysis machine in a CLiC device housing, which is a component of the 2008T dialysis machine that non-invasively measures hematocrit, percent change in blood volume and oxygen saturation in real time. The VND detection sensor system includes a PZT ultrasonic transmitter and receiver, as described above. The system transmits a frequency sweep around the resonance frequency of the crystal (3 MHz) to locate the frequency that elicits the largest amplitude response. The system then transmits at this frequency and measures the changes in the phase between the transmit and receive signals caused by pressure or sound speed changes inside the blood line. As discussed above, by measuring the phase changes, a VND event can be detected, and in some cases as well as various other signatures which arise from the operation of the dialysis machine, such as those caused by the actions/movements of the patient.

Hereinbelow, examples of the signatures in the VND data measurements during the dialysis procedure will be described with reference to FIGS. 11-20.

Figure 11:
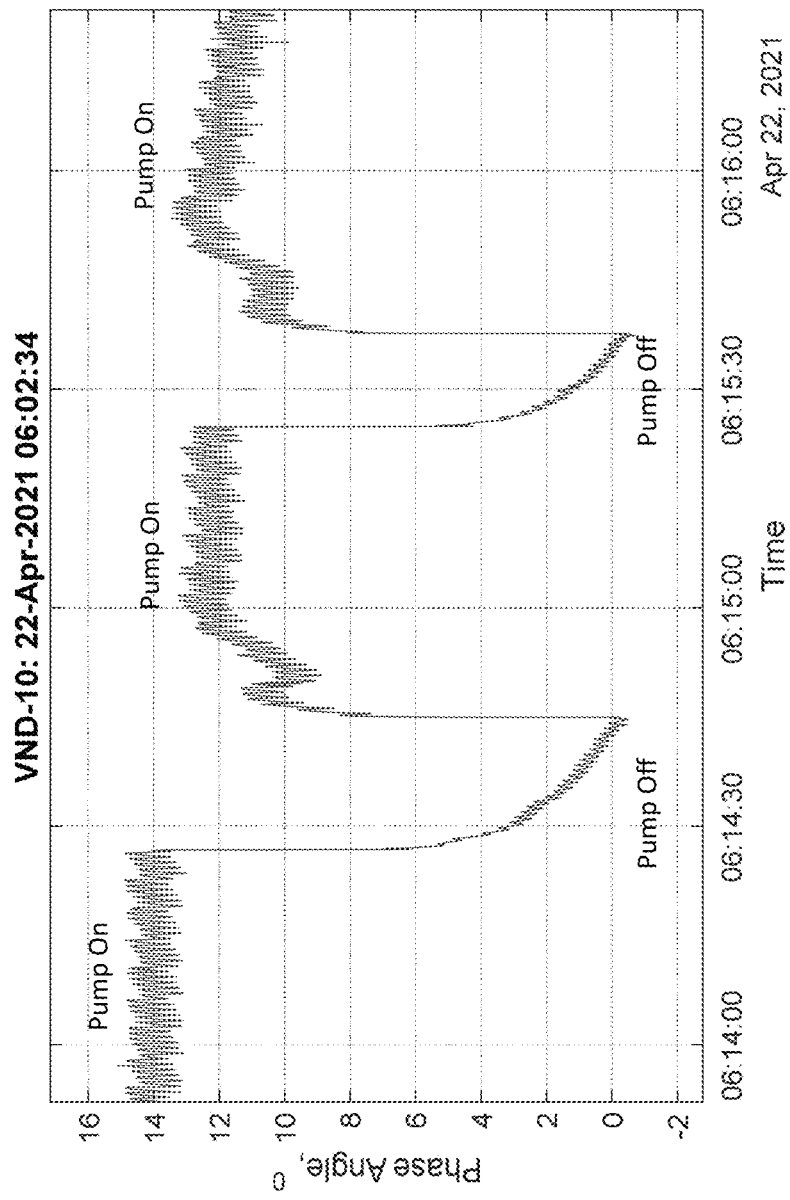
FIG. 11 depicts an example of a signature associated with the arterial pump turning on and off detected by the VND detection system according to the present teachings.

FIG. 11 depicts an example of a signature associated with the arterial pump turning on and off, which was detected by the VND system discussed above. As shown in FIG. 11, during the data collection, in response to turning off the arterial pump, the phase signal exhibited an initial drop by about 10°/sec, followed by a more gradual decrease by about 0.25°/sec. In contrast, the phase signal exhibited a sharp increase in response to the switching of the arterial pump from an off state into an on state. Thus, the phase signal exhibits a distinct signature indicative of the operational state of the pump.

Figure 12:
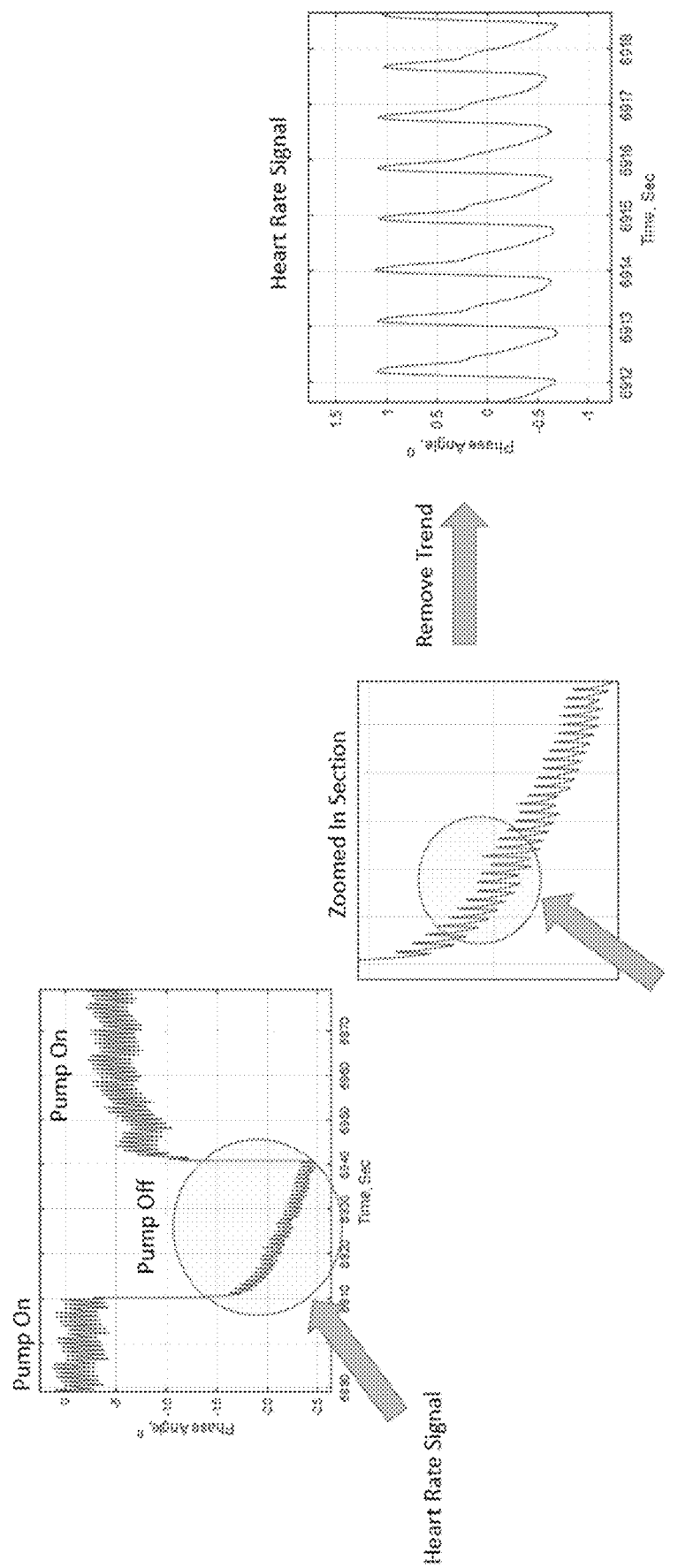
FIG. 12 depicts detection of the heart rate signal based on the VND detection system according to the present teachings.

In addition to signatures associated with the operation of the dialysis machine, in some embodiments, a VND sensor according to the present teachings can provide a signature associated with patient's heart rate. By way of example, as shown in FIG. 12, a heart rate signal can be readily observed when the arterial pump was turned off.

Figure 13:
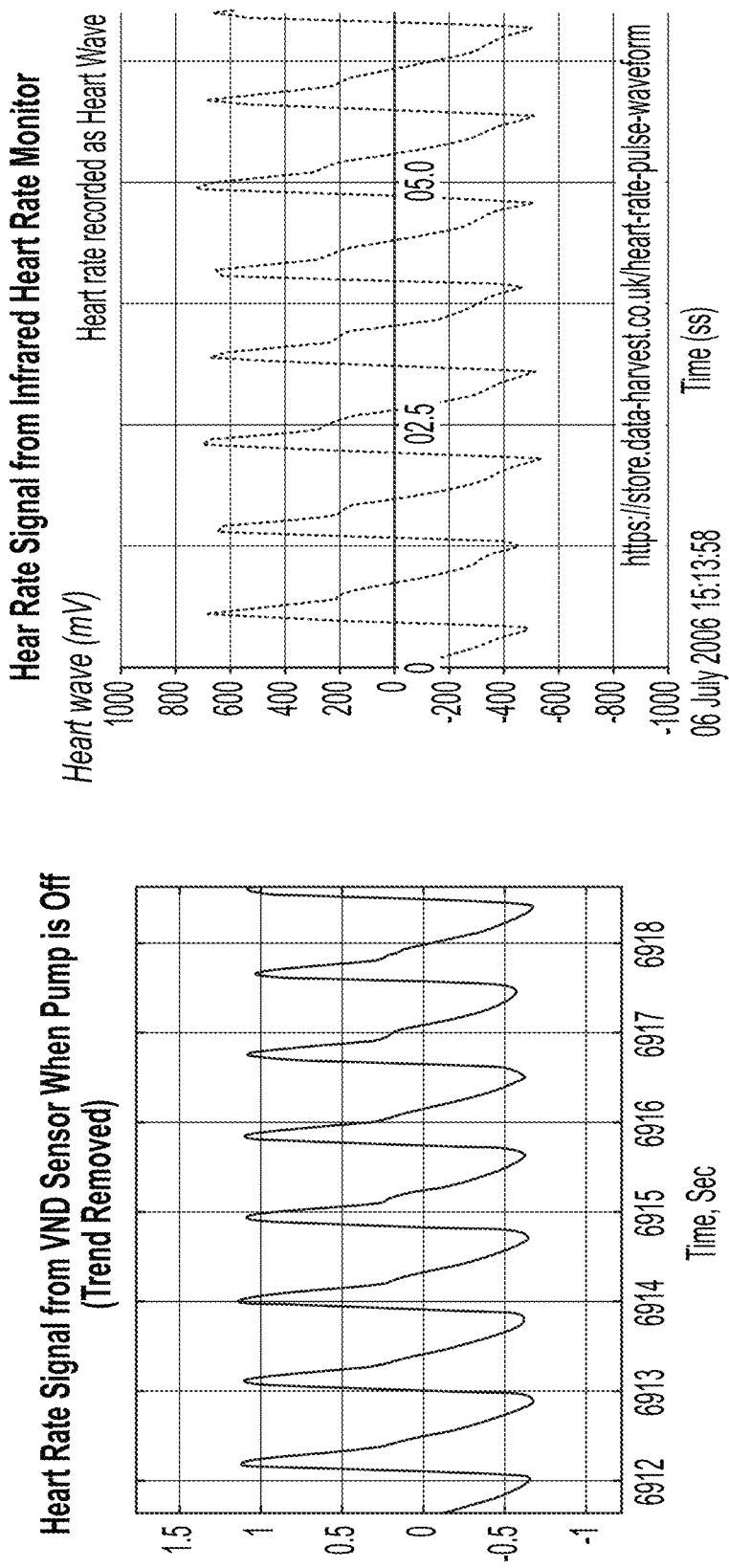
FIG. 13 compares the heart rate signal measured by the VND detection system according to the present teachings with that measured by an infrared heart rate monitor.
Figure 14:
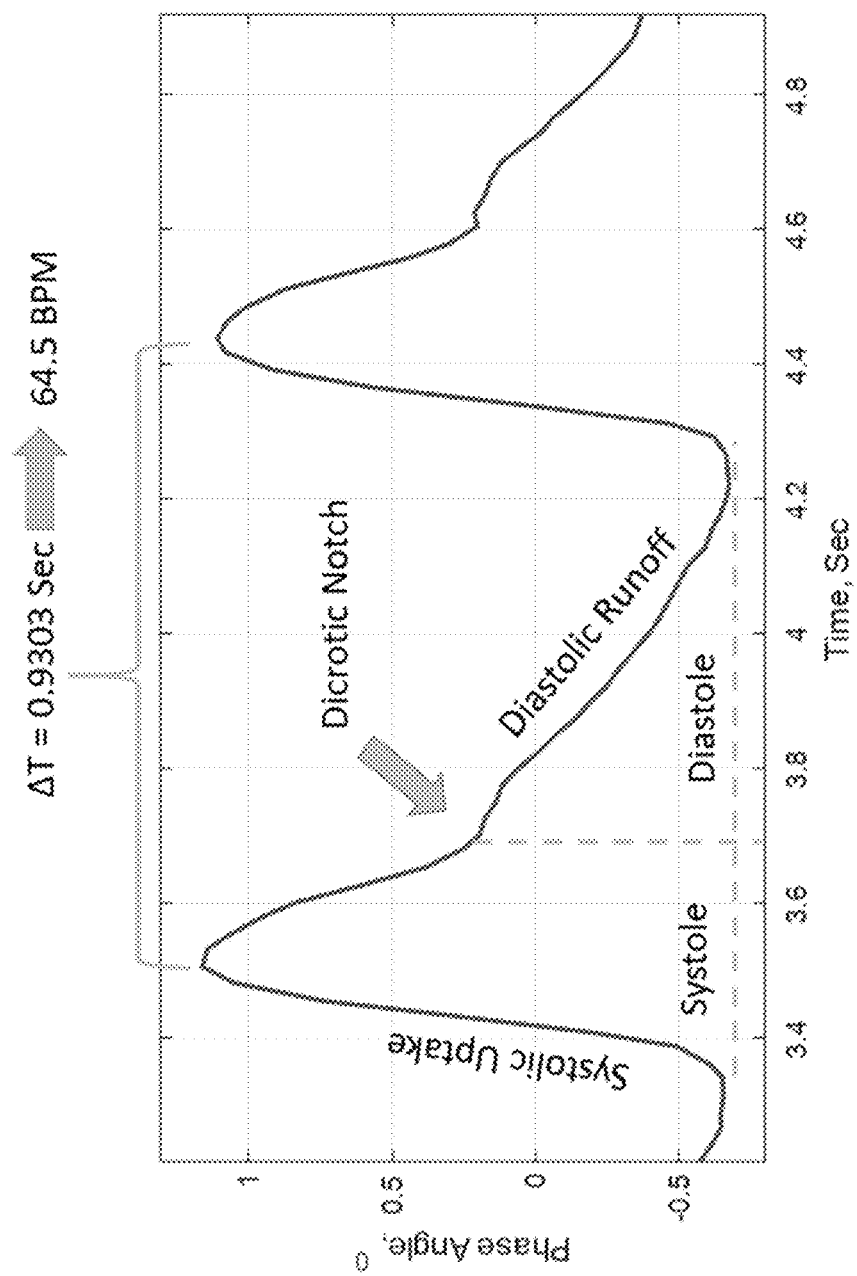
FIG. 14 shows features of a cycle of typical heart rate signal.

FIG. 13 compares the heart rate signal measured by the VND detection system with that measured by an infrared heart rate monitor, and FIG. 14 shows more detailed features associated with a cycle of typical heart rate signal. Referring to FIGS. 13 and 14, it can be seen that the VND detection system used in this example was capable of precise monitoring of the heart rate when the arterial pump was off.

Figure 15A:
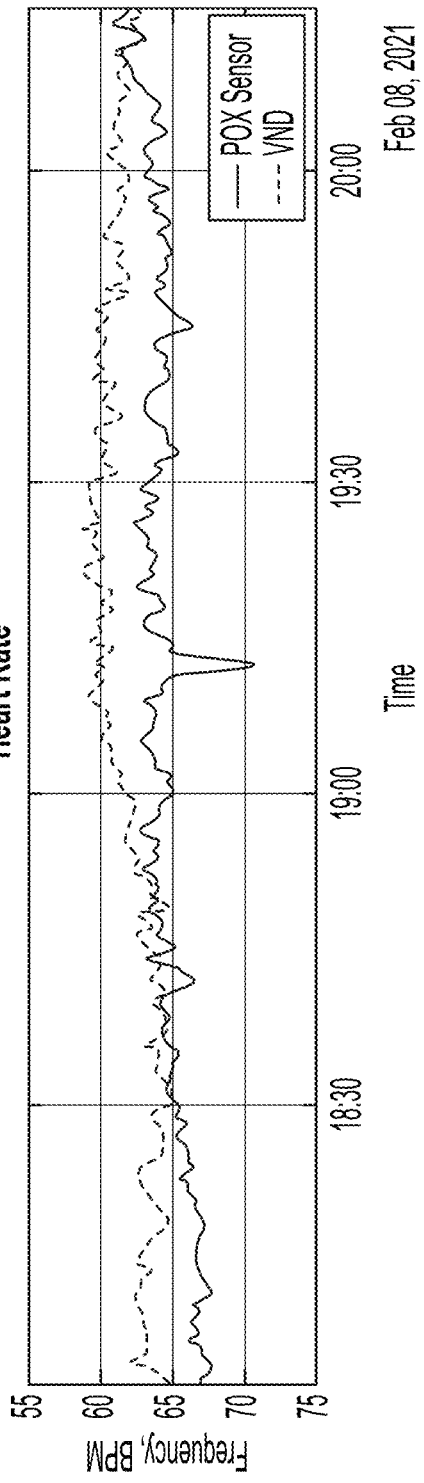
FIG. 15A compares the heart rate signal detected with the arterial pump running against the heart rate measured by a pulse oximeter sensor worn by a patient.
Figure 15B:
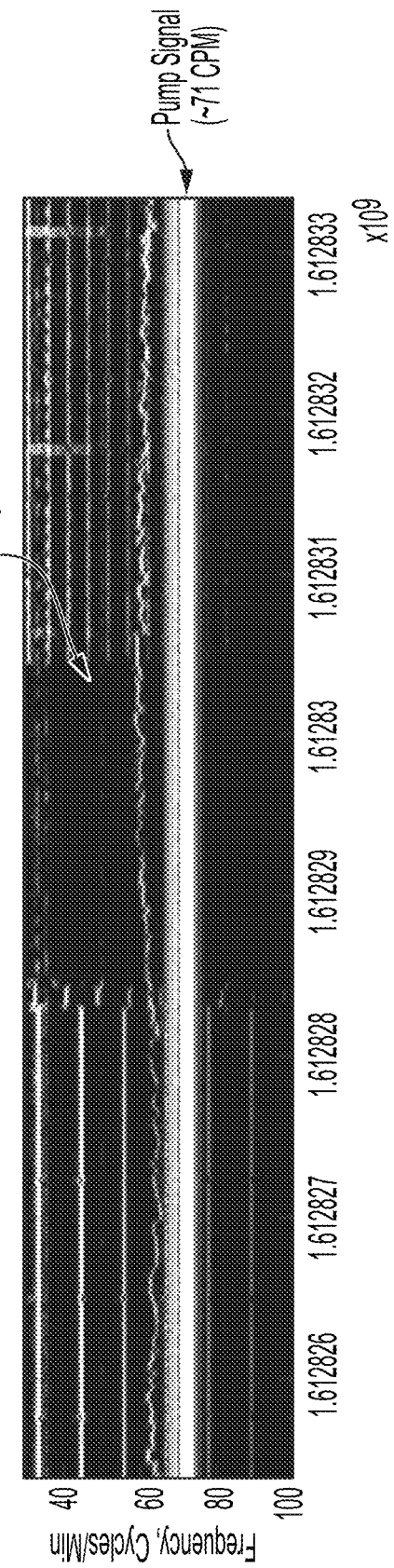
FIG. 15B is the corresponding time-frequency data showing the heart rate signal as well as the arterial pump signal.

FIGS. 15A and 15B illustrate that it was also feasible to detect a subject's heart rate signal while the arterial pump was running. FIG. 15A compares a heart rate signal detected with the arterial pump running with the heart rate measured by a pulse oximeter sensor worn by the patient. FIG. 15B is the corresponding time-frequency data showing the heart rate signal as well as the arterial pump signal. In this plot, brighter colors indicate a high amplitude level, while darker colors indicate a weaker signal. Herein, the heart rate signal was extracted using a STFFT (Short Time Fast Fourier Transform) method. However, the present teachings are not limited to the STFFT method, and various other data processing methods can be used to extract the heart rate signal within a couple of cycles of the heart rate (e.g., about 2 to 3 seconds).

Figures 16A, 16B:
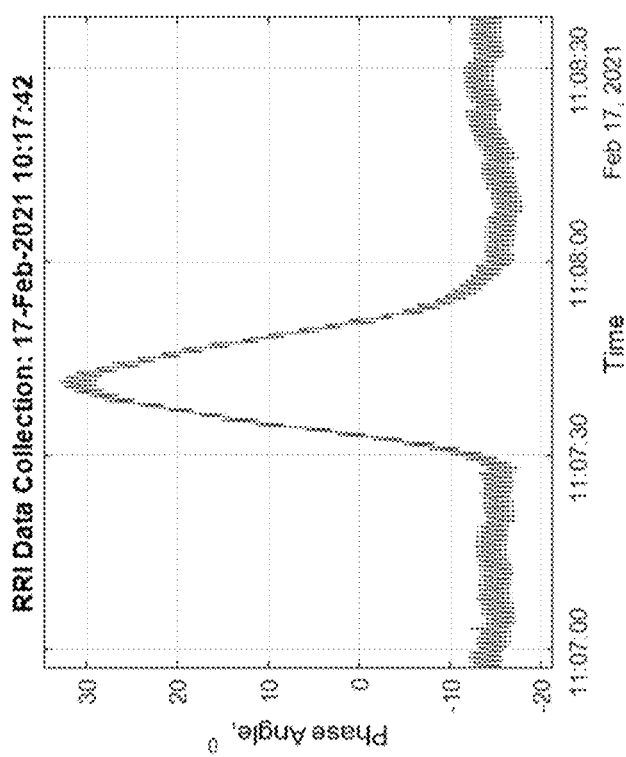
FIG. 16A shows a portion of a daily log of the dialysis treatment with an injection of medication (e.g., Mircera) introduced before the venous drip chamber.
FIG. 16B shows a signal response to the injection of medication.

FIGS. 16A and 16B show, respectively, a daily log of the dialysis treatment and a signal response to an injection of medication (e.g., Mircera) introduced before the venous drip chamber. As shown in FIG. 16B, the injection of medication produces a smoothly varying positive phase shift, which is discernable above the typical pump signal.

Figure 17:
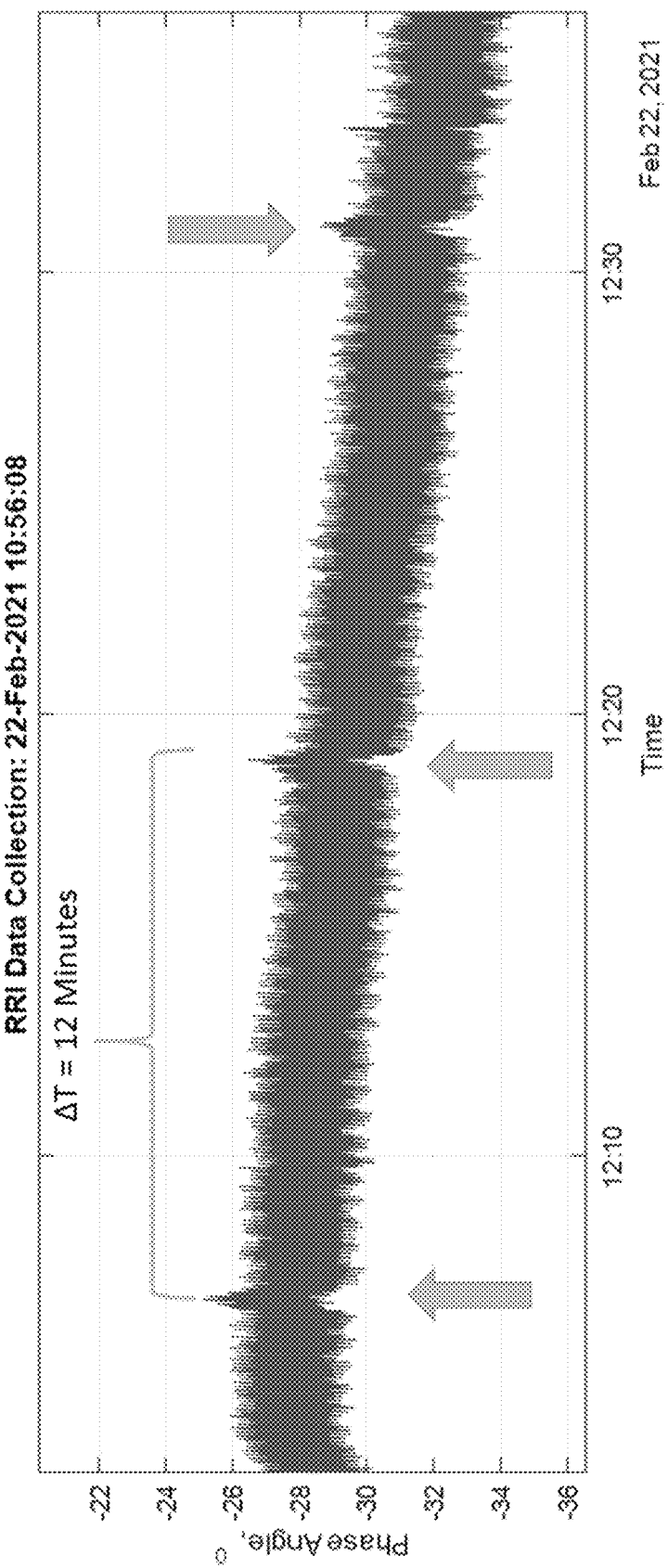
FIG. 17 shows a signature from an automated pressure hold test.

FIG. 17 shows a signature from an automated pressure hold test. In FIG. 17, small increases can be seen in the phase angle, occurring at about 12-minute intervals, providing a signature that is indicative of an automated pressure hold test performed by the dialysis machine.

Figure 18B:
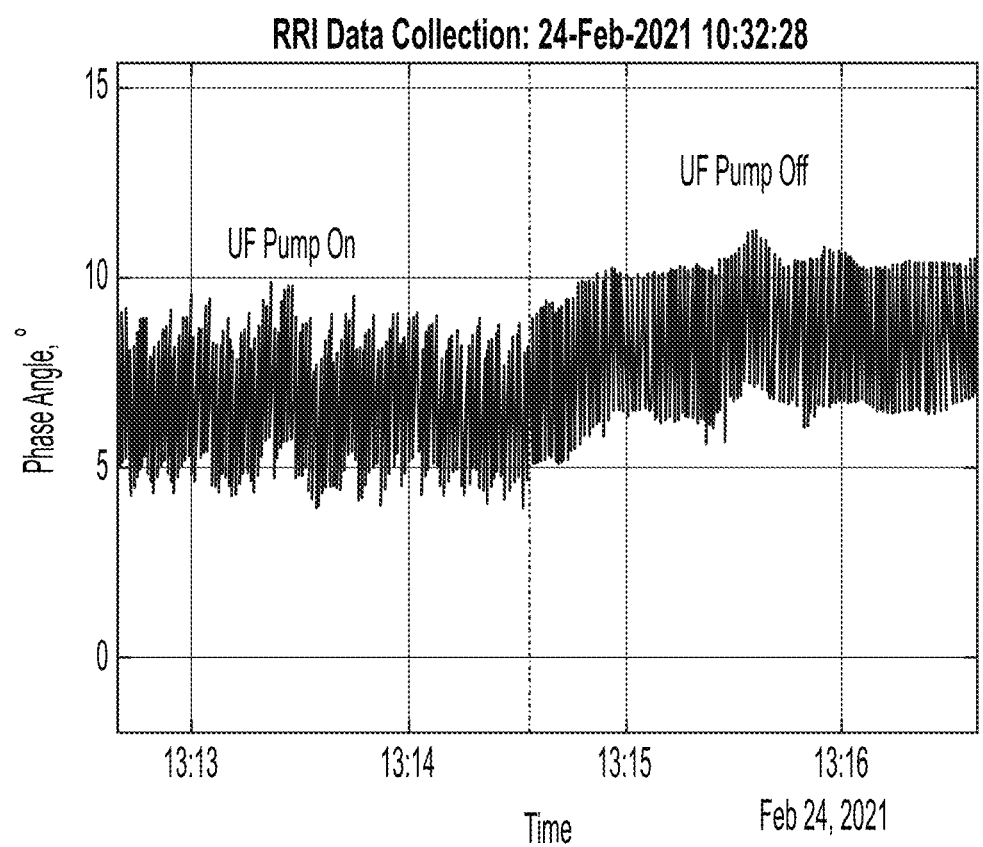
FIG. 18B shows the ultra filtration (UF) pump signal that interacts with the arterial pump signature to produce a characteristic beat frequency.

Referring to FIGS. 18A and 18B, the measured signals can show the ultra filtration (UF) pump signal that interacts with the arterial pump signature to produce a characteristic beat frequency. The first half of FIG. 18B represents the signal with an on state of the UF pump, where the characteristic beat frequency is visible. At approximately 13:14, the UF pump is turned off (see FIG. 18A), and the beat frequency disappears. In some embodiments, such a signature may be employed to discern the operational state of the UF pump.

Figure 19:
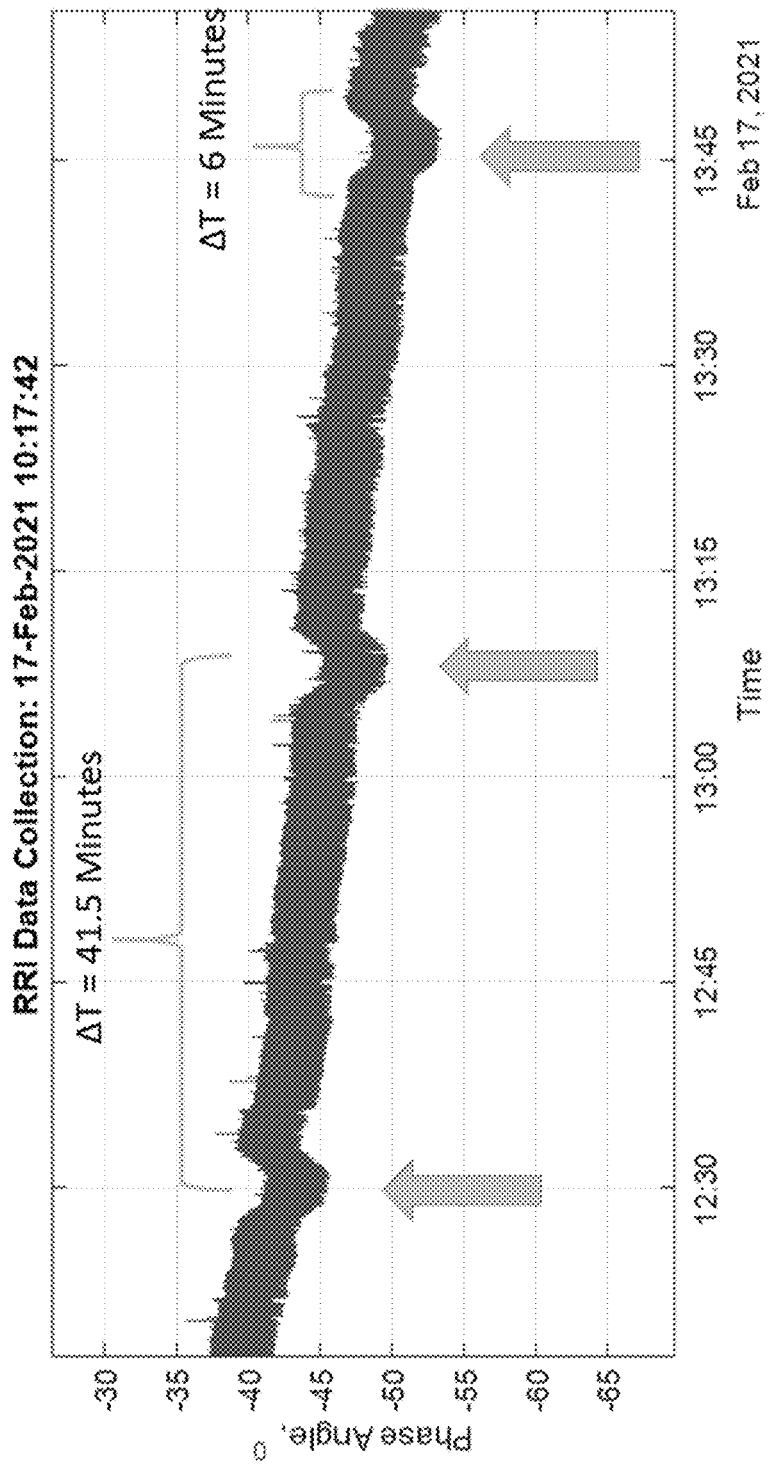
FIG. 19 shows the signal associated with the automated access flow bolus.

FIG. 19 shows a signal associated with the automated access flow bolus (e.g., due to the injection of saline bolus for automated conductivity test performed by the dialysis machine). In FIG. 19, a decrease in the phase data by a few degrees (e.g., by about 2°), occurring approximately every 41.5 minutes and lasting 6 minutes, can be seen, due to the automated access flow bolus.

Figure 20:
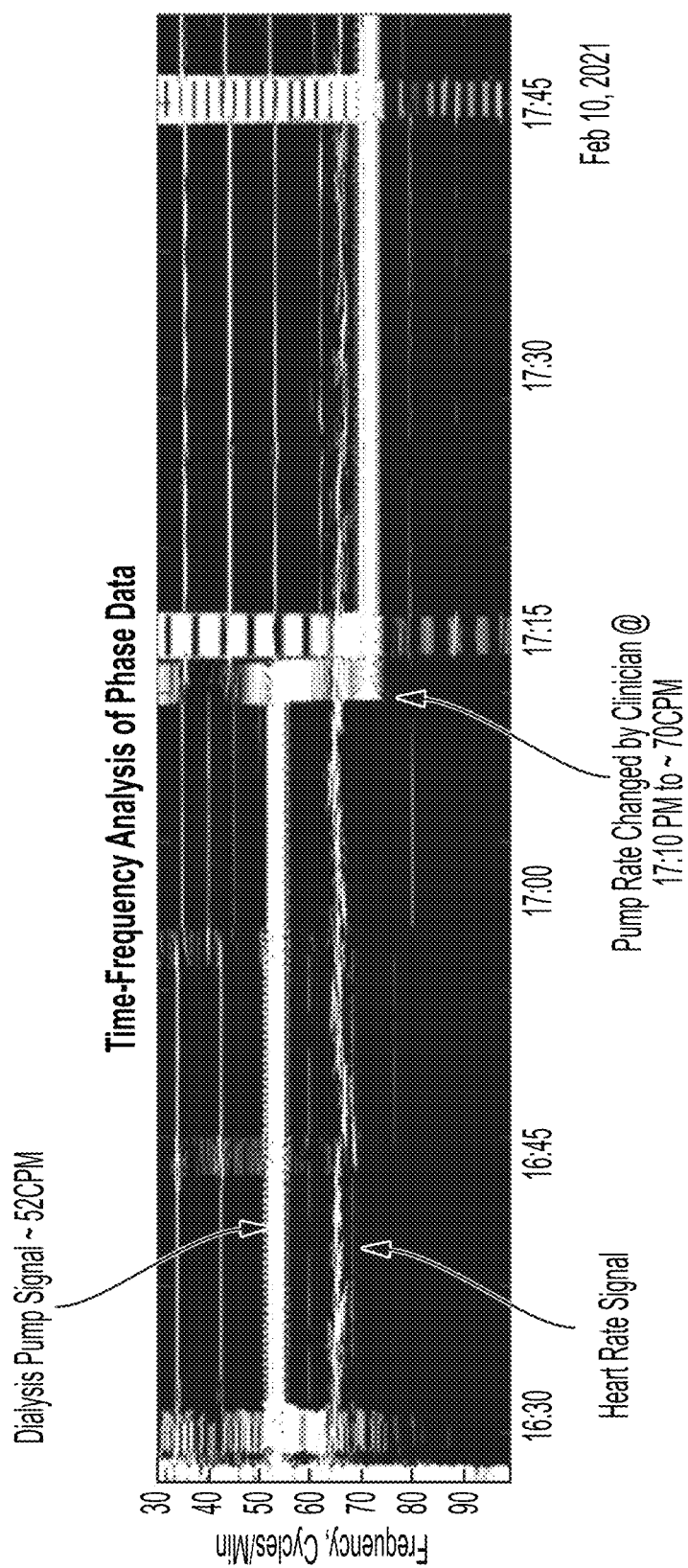
FIG. 20 shows the frequency content of the phase signal in response to a change of pumping rate.

FIG. 20 shows a signal response to a change of pumping rate. The signal was produced using the same STFFT method as described above for the heart rate detection with the pump running. In FIG. 20, it can be seen that the pump rate was increased from 52 CPM to 72 CPM (i.e., 300 to 400 mL/min) at approximately 17:10.

Figure 21B:
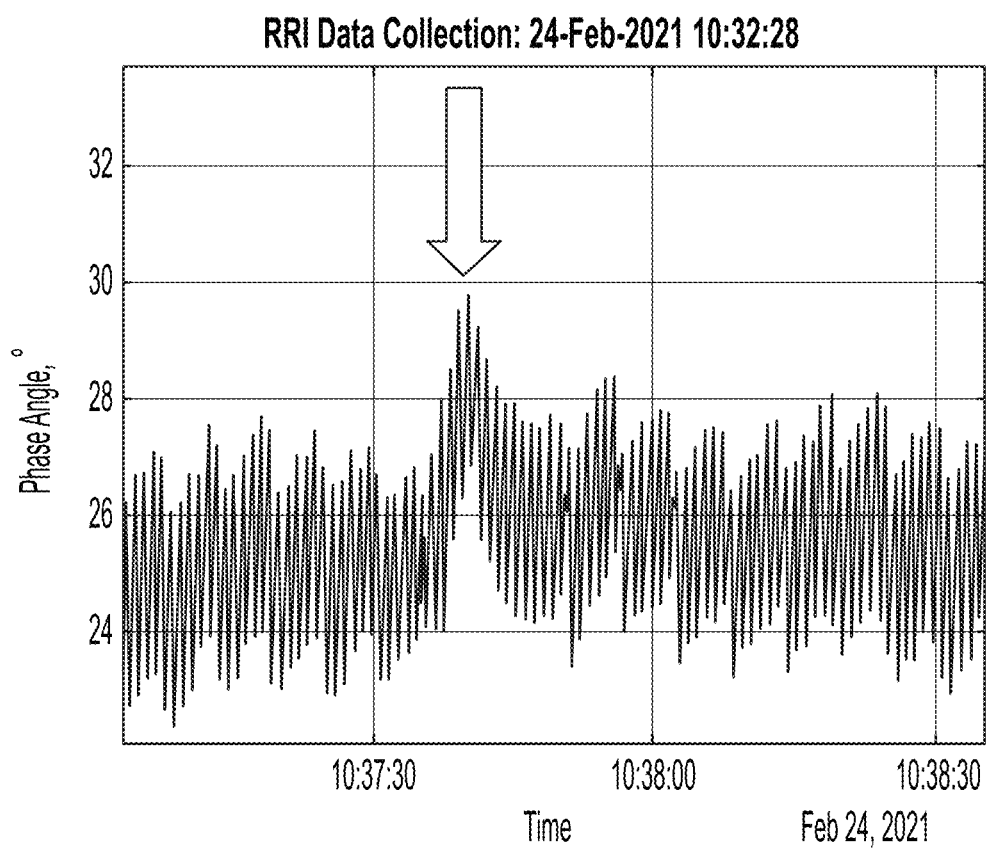
FIG. 21B shows a signal response to the injection of Heparin.

FIGS. 21A and 21B show, respectively, a portion of a daily log of a dialysis treatment and a signal response to an injection of heparin. As shown in FIG. 21B, the injection of medication produces a smoothly varying positive phase shift, which is discernable above the typical pump signal.

Figure 22B:
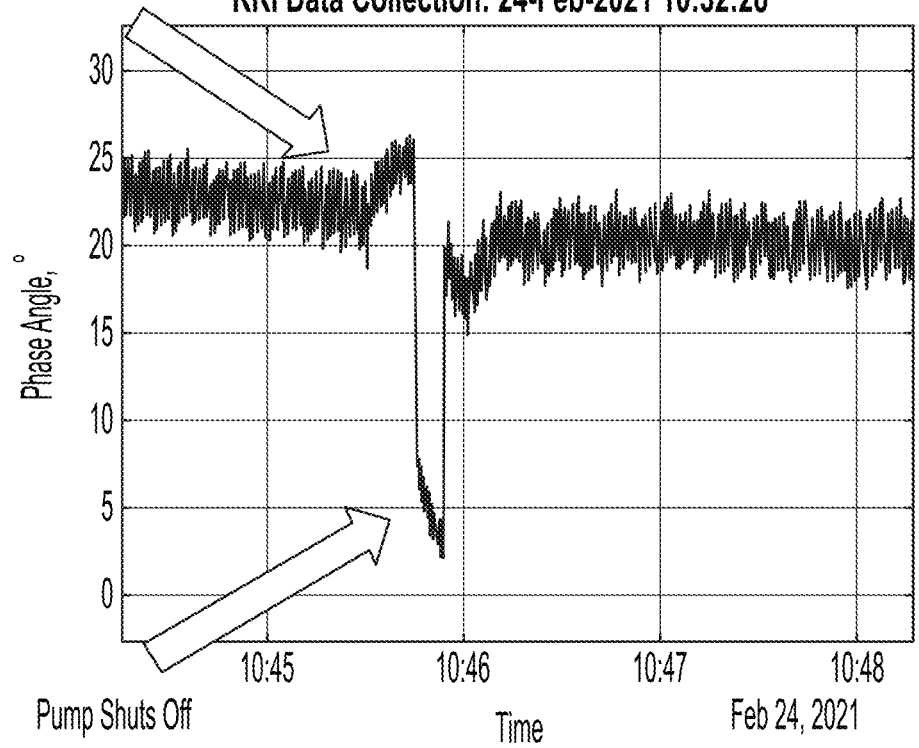
FIG. 22B shows a signal response to the injection of medication and the pump shut down.

FIGS. 22A and 22B show, respectively, a portion of a daily log of the dialysis treatment and a signal response to an injection of medication (e.g., Hectorol) followed by an arterial pressure alarm triggering the arterial pump to shut down. As shown in FIG. 22B, the injection of medication produces a smoothly varying positive phase shift, which is discernable above the typical pump. The phase signal exhibited an initial drop in response to the pump shut down similar to the phase signal signature shown in FIG. 11. As described above with reference to FIGS. 11-20, the VND detection technique according to the present teachings can provide sufficient sensitivity, reliability, and repeatability to discern not only a VND event, but also a variety of other events (e.g., the operational state of one or more pumps, medication injection, and patient arm movement), thereby allowing the discrimination of an VND event from other events. This can in turn help reduce the probability of false alarms.

In some embodiments, communication of data (e.g., inputs and outputs) between the dialysis system and the VND detection system may be bidirectional. For example, the VND detection system may transmit to the dialysis system one or more outputs (e.g., VND alarm, VND raw data (e.g., phase angle)), and the VND detection system may receive one or more inputs from the dialysis system (e.g., dialysate temperature, dialysate conductivity, TMP, arterial pressure, venous pressure, UF rate, dialysate flow bypass, BTM arterial and venous temperature, Hct, blood pressure, voltages, and dialysis machine alarms (e.g., blood leak, arterial pressure, venous pressure, TMP, dialysate temperature, dialysate conductivity, blood pump stop, heparin stop, and air detection)). In addition to the data identified above, the dialysis system and the VND detection system may be configured to receive and transmit between the two system other data (e.g., a clinician inputs, medication administrations, etc.). In such embodiments, this data available to the two systems (VND detection system and dialysis system) can be employed to enhance the sensitivity and/or the specificity of VND detection, and in particular, to reduce the probability of false alarms. By way of example, a VND identification algorithm can use inputs (e.g., UF pump shut down or medication administration) to anticipate and/or verify changes in the phase signal that are not VND events.

Example 3—Retrofitting a VND Sensor into a Dialysis Machine and Combining the VND Sensor with a Blood Sensed Sensor In some embodiments, a VND detection sensor according to the present teachings can be retrofitted into an existing dialysis machine, such as model 2008T or 5008S dialysis machines marketed by Fresenius Medical Care.

Figure 23:
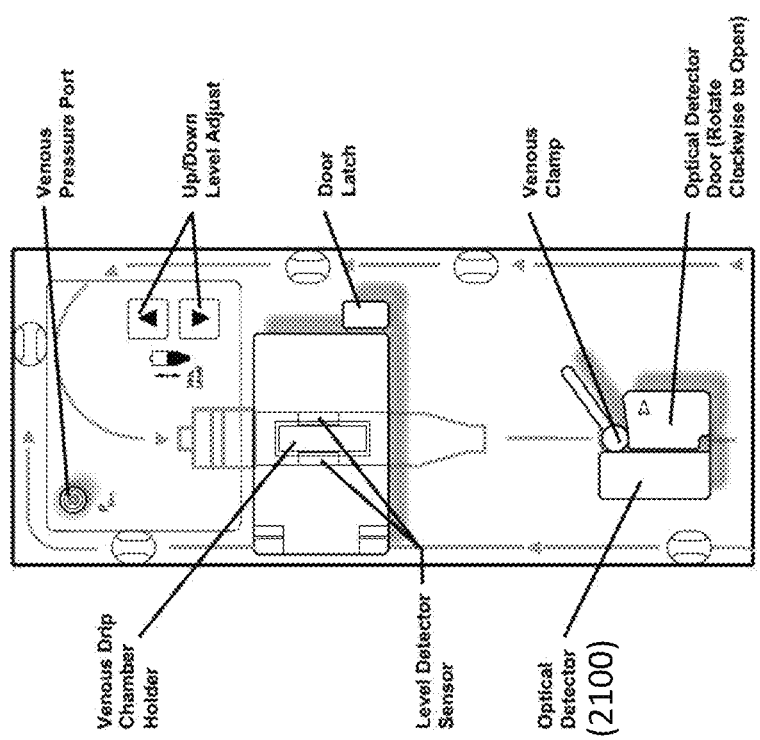
FIG. 23 depicts a 2008T dialysis machine schematic with an optical detector.

By way of example, FIG. 23 depicts a front panel of the 2008T dialysis machine equipped with an optical detector 2100 that optically distinguishes opaque fluid flow (e.g., blood) and clear fluid flow (e.g., saline).

In some embodiments, the VND detection sensor according to the present teachings can be integrated with an optical detector. By way of illustration, FIGS. 24 and 25 show an example of the VND detection sensor 2300 and an optical detector 2100, which are integrated into the same housing 2110.

Figure 24:
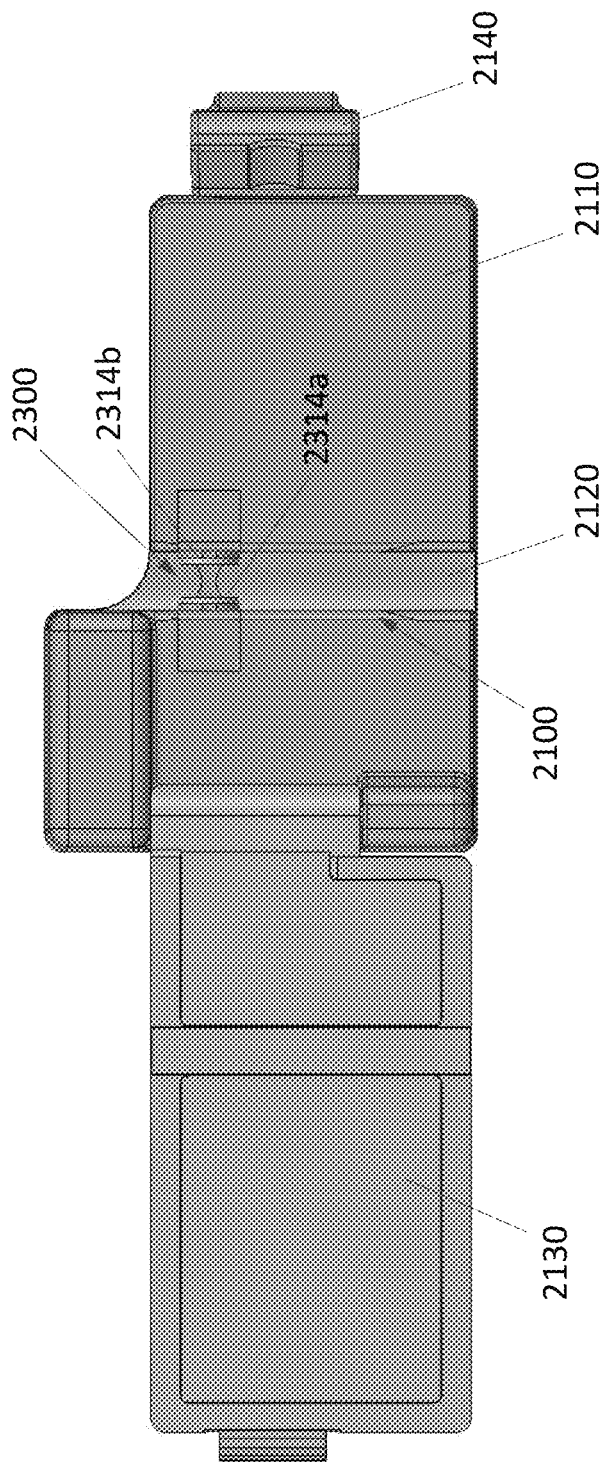
FIGS. 24 and 25 show an example of the VND detection sensor integrated into a same housing with the optical detector.
Figure 25:
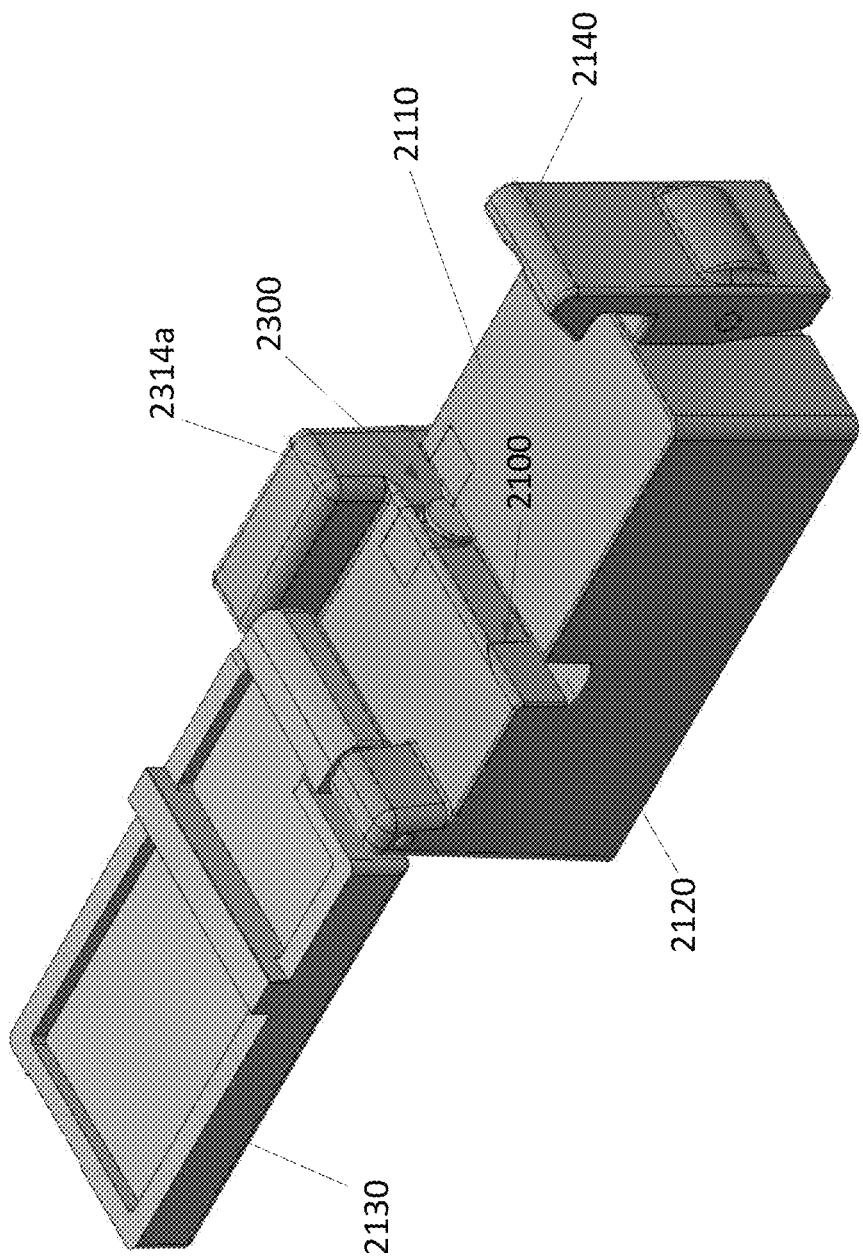

Referring to FIGS. 24 and 25, a pair of acoustic transmit/receive units 2314a and 2314b of the VND sensor 2300 are disposed in two opposed cavities provided in the opposed walls of a groove 2120, which is configured to receive a blood line. The transmit/receive units 2314a/2314b can be employed to establish a standing resonant acoustic wave in a portion of the blood flowing through the blood line as the blood passes between the transmit/receive units, in a manner discussed above.

As discussed above, the pair of acoustic transducer units 2314a and 2314b can be used to monitor a phase signal of the resonant acoustic wave to detect changes in the fluid dynamics of the flow within the blood line. In this embodiment, the structures and functions of the optical detector 2100 can be maintained unmodified. Further, a lid 2130 can be hingedly coupled to the housing 2110, and can be secured by a spring-biased latch 2140, such that a lid 2130 can retain the blood line within the groove 2120.

Figure 26:
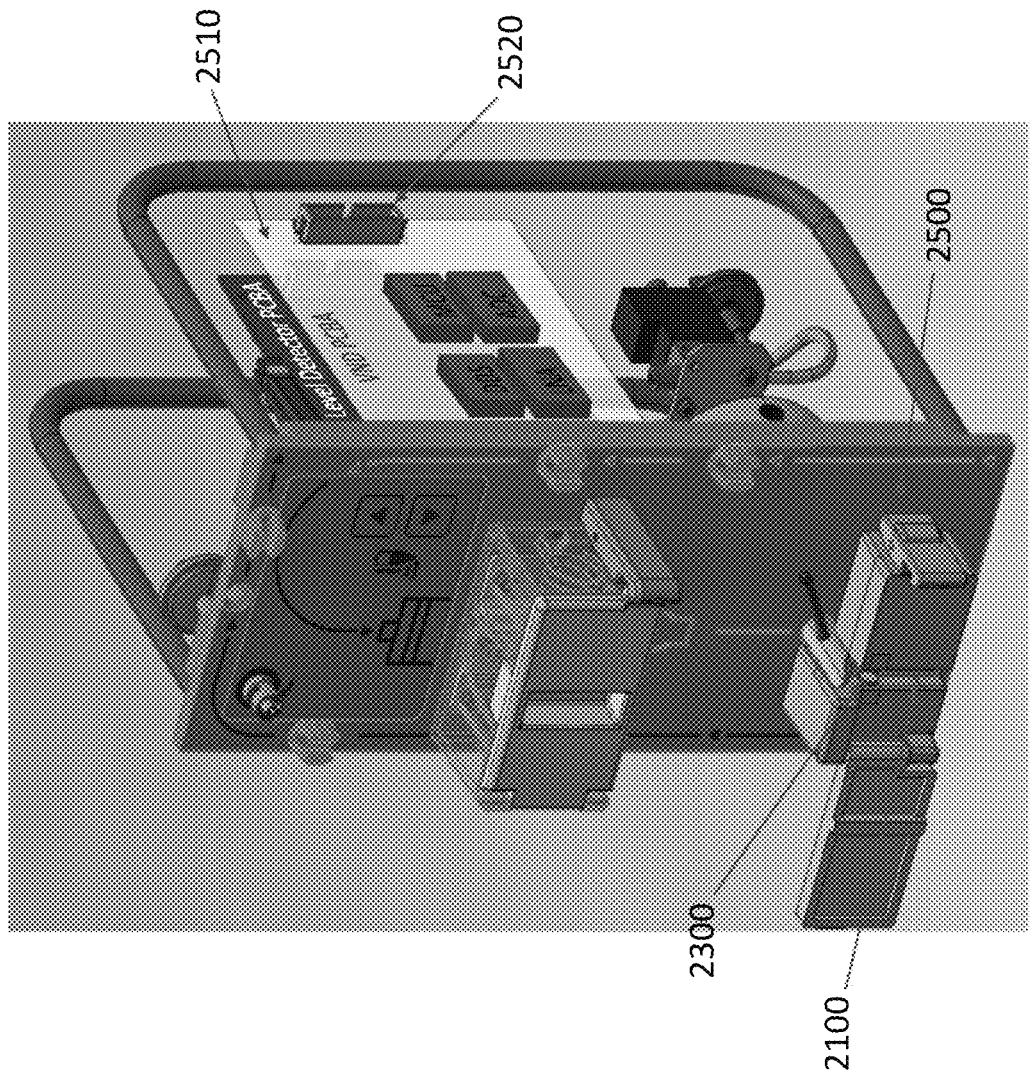
FIG. 26 shows an example of a sensor module including the VND detection sensor and the optical detector fitted into the 2008T dialysis machine.

FIG. 26 shows an example of a sensor module 2500 including the VND detection sensor 2300 and the optical detector 2100 retrofitted into the 2008T dialysis machine. A printed circuit board (PCB) 2510 can be added, e.g., adjacent to a level detector PCB, to support the operation of the VND retrofit sensor. To allow communication between the VND sensor and the main processor of the 2008T machine, a socket 2520 can be provided on the PCB 2510 to accommodate a communication cable (e.g., an RS-232 connector). In some embodiments, in order to make the sensor module more compact, the electronic components associated with the VND detection sensor 2300 can be included within the housing 2110 of the sensor module 2500, eliminating any need for an additional PCB 2510. In some embodiments, the sensor module 2500 can further include therein other sensors such as a blood sensed sensor, air bubble detector, electrolyte sensor, venous pressure transducer, temperature sensor, or the like, such that the additional data can be employed to enhance the sensitivity and/or the specificity of VND detection, and in particular to reduce the probability of false alarms.

What is claimed is:

1. A method of detecting a change in fluid dynamics of a fluid flowing through an extra-corporeal circuit, comprising:
   establishing a resonant standing acoustic wave substantially perpendicular to said fluid flow across at least a portion of a line associated with said extra-corporeal circuit through which said fluid flows, wherein the step of establishing the resonant standing acoustic wave comprises transmitting an acoustic wave into said portion of the line substantially perpendicular to said fluid flow and detecting at least a portion of the acoustic wave after its passage through said flowing fluid;
   monitoring a phase signal corresponding to a difference between a phase of said transmitted acoustic wave and a phase of said detected acoustic wave and
   identifying occurrence of a change in the fluid dynamics of said flowing fluid when the monitored phase signal of said resonant acoustic wave indicates a deviation from an expected phase signature associated with the fluid flow; wherein said change in the fluid dynamics is caused by at least partial dislodgement of another portion of said line.

2. The method of claim 1, wherein said extra-corporeal circuit comprises an extra-corporeal dialysis circuit and said line is a venous return line.

3. The method of claim 1, wherein said expected phase signature comprises a phase signature associated with heartbeats of a patient coupled to said extra-corporeal circuit.

4. The method of claim 2, wherein said deviation of said monitored phase signal comprises a substantial disappearance of said signature of the phase signal, indicating a substantially complete dislodgement of said venous return line.

5. The method of claim 1, wherein said acoustic wave has a single frequency in a range of about 1 MHz to about 20 MHz.

6. The method of claim 1, further comprising changing frequency of said resonant standing acoustic wave and monitoring a shift in said phase signal as a function of frequency to identify an optimal frequency for said resonant standing acoustic wave,
   wherein said step of changing the frequency of the resonant standing acoustic wave comprises applying a frequency modulation to said resonant standing acoustic wave.

7. The method of claim 1, wherein said deviation from the expected phase signature is caused by an inconsistent flow rate of the fluid.

8. The method of claim 1, wherein said fluid is blood and further comprising adjusting a flow rate of the blood in response to detection of said change in the fluid dynamics of the flowing fluid.

9. A system for detecting a change in fluid dynamics of a fluid flowing in a line associated with an extra-corporeal circuit, comprising:
   an acoustic wave transmitter for establishing a resonant acoustic standing wave substantially perpendicular to said fluid flow across a lumen of said line such that the resonant acoustic standing wave travels through a portion of the fluid traversing through said lumen;
   a detector for detecting at least a portion of said resonant acoustic standing wave after its passage through said fluid;
   a phase detector for measuring a phase signal indicative of a phase difference between the transmitted acoustic wave and the detected acoustic wave; and
   a comparator for comparing the measured phase signal with an expected phase signature associated with the fluid dynamics of said fluid flowing through said line,
   wherein a deviation identified by said comparator between the measured phase signal and the expected phase signature indicates occurrence of an at least partial dislodgement of at least a portion of said line.

10. The system of claim 9, further comprising an analyzer for correlating said deviation to an event causing the change in the fluid dynamics, wherein said analyzer is configured to analyze said phase deviation so as to identify said event as an at least partial dislodgement of at least a portion of said line from an expected position.

11. The system of claim 9, wherein said acoustic wave transmitter is configured to generate an acoustic wave with a single frequency in a range of about 1 MHz to about 20 MHz.

12. The system of claim 10, wherein said analyzer is configured to identify a deviation of said phase signal corresponding to at least partial dislodgement of said venous return line.

13. The system of claim 10, wherein said analyzer is configured to correlate a substantial disappearance of said phase signal with a substantially complete dislodgement of said venous return line.

14. The system of claim 9, wherein any of said acoustic wave transmitter and said detector is releasably coupled to said line with a spring-load clamp.

15. A dialysis system, comprising:

a dialyzer;

an arterial line for providing a path for blood flow from a patient's circulatory system to an inlet port of the dialyzer;

a venous blood line for providing a path for flow of blood exiting the dialyzer to the patient's circulatory system; and an acoustic sensor coupled to said venous blood line, wherein said acoustic sensor is configured to:

establish an acoustic standing wave in a portion of the venous blood line substantially perpendicular to blood flow, detect at least a portion of the acoustic standing wave after passage of the acoustic wave through the flow of blood, and monitor a phase signal associated with said acoustic wave, said phase signal corresponding to a difference between a phase of said transmitted acoustic wave and a phase of said detected acoustic wave, and wherein a deviation of said monitored phase signal relative to an expected phase signature indicates at least a partial dislodgement of the venous blood line.

* * * * *